US010584183B2

(12) United States Patent
Sannino et al.

(10) Patent No.: US 10,584,183 B2
(45) Date of Patent: *Mar. 10, 2020

(54) METHOD FOR PRODUCING HYDROGELS COUPLING HIGH ELASTIC MODULUS AND ABSORBANCE

(71) Applicant: GELESIS, LLC, Boston, MA (US)

(72) Inventors: Alessandro Sannino, Lecce (IT); Christian Demitri, San Pietro in Lama (IT); Yishai Zohar, Brookline, MA (US); Eyal S. Ron, Lexington, MA (US); Barry J. Hand, Acton, MA (US); Cosimo Saponaro, Cavallino (IT)

(73) Assignee: Gelesis, LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/220,598

(22) Filed: Dec. 14, 2018

(65) Prior Publication Data

US 2019/0233545 A1    Aug. 1, 2019

Related U.S. Application Data

(63) Continuation of application No. 15/010,626, filed on Jan. 29, 2016, now Pat. No. 10,179,824.

(60) Provisional application No. 62/109,392, filed on Jan. 29, 2015.

(51) Int. Cl.
| C08B 15/00 | (2006.01) |
| A61K 31/738 | (2006.01) |
| A61K 9/00 | (2006.01) |
| A61K 9/48 | (2006.01) |

(52) U.S. Cl.
CPC .......... *C08B 15/005* (2013.01); *A61K 9/0053* (2013.01); *A61K 9/4866* (2013.01); *A61K 31/738* (2013.01)

(58) Field of Classification Search
None
See application file for complete search history.

(56) References Cited

U.S. PATENT DOCUMENTS

| 3,526,048 A | 9/1970 | Rowland et al. |
| 5,137,537 A | 8/1992 | Herron et al. |
| 5,247,072 A | 9/1993 | Ning et al. |
| 5,415,864 A | 5/1995 | Kopecek et al. |
| 5,550,189 A | 8/1996 | Qin et al. |
| 5,800,418 A | 9/1998 | Ahr |
| 5,873,979 A | 2/1999 | Naieni et al. |
| 6,271,278 B1 | 8/2001 | Park et al. |
| 6,436,441 B1 | 8/2002 | Sako et al. |
| 6,471,824 B1 | 10/2002 | Jewell et al. |
| 6,630,422 B1 | 10/2003 | Sannino et al. |
| 6,686,464 B1 | 2/2004 | Harding et al. |
| 6,765,042 B1 | 7/2004 | Besemer et al. |
| 7,071,327 B2 | 7/2006 | Mensitieri et al. |
| 8,658,147 B2 | 2/2014 | Nicolais et al. |
| 9,353,191 B2 | 5/2016 | Sannino et al. |
| 2001/0006677 A1 | 7/2001 | McGinity et al. |
| 2003/0144642 A1 | 7/2003 | Dopps et al. |
| 2004/0157734 A1 | 8/2004 | Mertens et al. |
| 2005/0100603 A1 | 5/2005 | Sako et al. |
| 2005/0118326 A1 | 6/2005 | Anfinsen et al. |
| 2005/0143571 A1 | 6/2005 | Stoyanov et al. |
| 2006/0102483 A1 | 5/2006 | Chuang et al. |
| 2006/0142478 A1 | 6/2006 | Luo et al. |
| 2006/0142480 A1 | 6/2006 | Luo et al. |
| 2007/0231366 A1 | 10/2007 | Sawhney et al. |
| 2008/0009616 A1 | 1/2008 | Frank et al. |
| 2008/0095911 A1 | 4/2008 | Adams et al. |
| 2008/0103228 A1 | 5/2008 | Falcone et al. |
| 2008/0147026 A1 | 6/2008 | Qin et al. |
| 2008/0166410 A1 | 7/2008 | Funk et al. |
| 2008/0227944 A1 | 9/2008 | Ambrosio et al. |
| 2008/0241094 A1 | 10/2008 | Burnett et al. |
| 2008/0262155 A1 | 10/2008 | Mertens et al. |
| 2009/0099541 A1 | 4/2009 | Qin et al. |
| 2009/0311235 A1 | 12/2009 | Elenko et al. |
| 2009/0324537 A1 | 12/2009 | Bucevschi et al. |
| 2010/0234233 A1 | 9/2010 | Sannino et al. |
| 2012/0052151 A1 | 3/2012 | Sannino et al. |
| 2013/0089737 A1 | 4/2013 | Sannino et al. |

(Continued)

FOREIGN PATENT DOCUMENTS

| CA | 2812246 A1 | 10/2013 |
| DE | 212969 | 8/1984 |
| DE | 19654745 A1 | 7/1998 |

(Continued)

OTHER PUBLICATIONS

"MP Biomedicals Technical Information for Carboxymethyl cellulose Sodium Salt", 2010.
"Prevention", in Glossary of medical education terms: Parts 1-7. Wojtczak, A., Ed. Medical Teacher. vol. 24, Nos. 2-6 and vol. 25, No. 1 & 2, 2002.
"Walocel™ C reference 2014", 2014.
Anbergen, et al., "Elasticity and swelling behavior of chemically crosslinked cellulose ethers in aqueous systems", Polymer, 31, 1990, 1854-1858.
Capitani, et al., "13C Solid-State NMR Determination of Cross-Linking Degree in Superabsorbing Cellulose-Based Networks", Macromolecules, 33, 2000, 430-437.

(Continued)

*Primary Examiner* — Shaojia A Jiang
*Assistant Examiner* — Dale R Miller
(74) *Attorney, Agent, or Firm* — Elmore Patent Law Group, P.C.; Edgar W. Harlan; Carolyn S. Elmore

(57) ABSTRACT

The present invention provides crosslinked carboxymethylcellulose having high elastic modulus coupled with high absorbance capacity when swollen in simulated gastric fluid/water (1:8) and simulated intestinal fluids. The invention further provides methods of making the crosslinked carboxymethylcellulose, compositions comprising the crosslinked carboxymethylcellulose and methods of using the crosslinked carboxymethylcellulose, for example, for treating overweight or obesity or for enhancing glycemic control.

19 Claims, 6 Drawing Sheets

(56) References Cited

U.S. PATENT DOCUMENTS

2014/0296507 A1 10/2014 Sannino et al.
2015/0366898 A1 12/2015 Ron et al.

FOREIGN PATENT DOCUMENTS

| EP | 0637594 A2 | 8/1994 |
|---|---|---|
| JP | 2004010634 A | 1/2004 |
| JP | 2008069315 A | 3/2008 |
| JP | 2008285611 A | 11/2008 |
| WO | 1996/002276 A2 | 2/1996 |
| WO | 1999/026670 A1 | 6/1999 |
| WO | 2000/032064 A1 | 6/2000 |
| WO | 2001/087365 A2 | 11/2001 |
| WO | 2006/070337 A2 | 7/2006 |
| WO | 2007/112436 A2 | 10/2007 |
| WO | 2007/115169 A2 | 10/2007 |
| WO | 2009/021701 A2 | 2/2009 |
| WO | 2009/022358 A1 | 2/2009 |
| WO | 2010059725 A1 | 5/2010 |
| WO | 2014/074696 A1 | 5/2014 |

OTHER PUBLICATIONS

Casciaro, et al., "Experimental investigation and theoretical modelling of the nonlinear acoustical behaviour of a liver tissue and comparison with a tissue mimicking hydrogel", J. Mater Sci: Mater Med, 19, 2008, 899-906.
Casciaro, et al., "Full experimental modelling of a liver tissue mimicking phantom for medical ultrasound studies employing different hydrogels", J. Mater Sci: Mater Med, 20, 2009, 983-989.
Chang, et al., "Structure and properties of hydrogels prepared from cellulose in NaOH/urea aqueous solutions", Carbohydrate Polymers, 82, 2010, 122-127.
Chang, et al., "Superabsorbent hydrogels and based on cellulose for smart swelling and controllable delivery", European Polymer Journal, 46, 2010, 92-100.
Coma, et al., "Film properties from crosslinking of cellulosic derivatives with a polyfunctional carboxylic acid", Carbohydrate Polymers, 51, 2003, 265-271.
Demitri, et al., "Hydrogel Based Tissue Mimicking Phantom for In-Vitro Ultrasound Contrast Agents Studies", J. Biomed Mater Res Part B: Appl Biomater, 87B, 2008, 338-345.
Demitri, C. et al., "Novel Superabsorbent Cellulose-Based Hydrogels Crosslinked with Citric Acid", Journal of Applied Polymer Science, 110(4), Aug. 20, 2008, 2453-2460.
Esposito, et al., "Response of intestinal cells and macrophages to an orally administered cellulose-PEG based polymer as a potential treatment for intractable edemas", Biomaterials, 26, 2005, 4101-4110.
Esposito, F. et al., "Water Sorption in Cellulose-Based Hydrogels", Journal of Applied Polymer Science, 60, 1996, 2403-2407.
Gorgieva, et al., "Synthesis and application of new temperature-responsive hydrogels based on carboxymethyl and hydroxyethyl cellulose derivatives for the functional finishing of cotton knitwear", Carbohydrate Polymers, 85, 2011, 664-673.
Hashem, et al., "Synthesis and characterization of novel carboxymethylcellulose hydrogels and carboxymethylcellulose-hydrogel-ZnO-nanocomposites", Carbohydrate Polymers, 95(1), 2013, 421-427.
Hoogendam, C. W. et al., "Persistence length of carboxymethyl cellulose as evaluated from size exclusion chromatography and potentionmetric titrations", Macromolecules, 31, 1998, 6297-6309.
Ito, "The prevention of peritoneal adhesions by in situ cross-linking hydrogels of hyaluronic acid and cellulose derivatives", Biomaterials, 28:, 2007, 975-983.
Kadajji, V G. et al., "Water Soluble Polymers for Pharmaceutical Applications", Polymers 3, 2011, 1972-2009.

Kose, G. T. et al., "Macroporous poly(3-hydroxybutyrate-co-3-hydroxyvalerate) matrices for bone tissue engineering", Biomaterials, 24, 2003, 1949-1958.
Lenzi, et al., "Probing the degree of crosslinking of a cellulose based superabsorbing hydrogel through traditional and NMR techniques", Polymer, 44, 2003, 1577-1588.
Lionetto, et al., "Ultrasonic monitoring of the network formation in superabsorbent cellulose based hydrogels", Polymer, 46, 2005, 1796-1803.
Liu, et al., "Radiation crosslinking of CMC-Na at low dose and its application as substitute for hydrogel", Radiation Physics and Chemistry, 72, 2005, 635-638.
Liu, et al., "Radiation preparation and swelling behavior of sodium carboxymethyl cellulose hydrogels", Radiation Physics and Chemistry, 63, 2002, 525-528.
Marci, et al., "Environmentally sustainable production of cellulose-based superabsorbent hydrogels", Green Chem., 8, 2006, 439-444.
Ogushi, et al., "Synthesis of Enzymatically-Gellable Carboxymethylcellulose for Biomedical Applications", Journal of Bioscience and Bioengineering, 104(1), 2007, 30-33.
Qiu, et al., "Effect of activated carbon on the properties of carboxymethylcellulose/activated carbon hybrid hydrogels synthesized by γ-radiation technique", Carbohydrate Polymers, 70, 2007, 236-242.
Raucci, M. G. et al., "Effect of citric acid crosslinking cellulose-based hydrogels on osteogenic differentiation", Journal of Biomedical Materials Research, 103(6), 2014, 2045-2056.
Sannino, et al., "A Cellulose-Based Hydrogel as a Potential Bulking Agent for Hypocaloric Diets: An In Vitro Biocompatibility Study on Rat Intestine", Journal of Applied Polymer Science, 102, Jul. 28, 2006, 1524-1530.
Sannino, et al., "Biodegradable-Cellulose-based Hydrogels: Design and Applications", Materials, 2, 2009, 353-373.
Sannino, et al., "Biomedical application of a superabsorbent hydrogel for body water elimination in the treatment of edemas", J. Biomed. Mater Res., 67A, 2003, 1016-1024.
Sannino, et al., "Cellulose Derivative-Hyaluronic Acid-Based Microporous Hydrogels Cross-Linked through Divinyl Sulfone (DVS) to Modulate Equilibrium Sorption Capacity and Network Stability", Biomacromolecules, 5, 2004, 92-96.
Sannino, et al., "Cellulose-based hydrogels as body water retainers", J. Mater Sci: Mat in Med., 11, 2000, 247-253.
Sannino, et al., "Concurrent effect of microporosity and chemical structure on the equilibrium sorption properties of cellulose-based hydrogels", Polymer, 46, 2005, 4676-4685.
Sannino, et al., "Crosslinking of cellulose derivatives and hyaluronic acid with water-soluble carbodiimide", Polymer, 46, 2005, 11206-11212.
Sannino, et al., "Designing microporous macromolecular hydrogels for biomedical applications: a comparison between two techniques", Composites Science and Technology, 63, 2003, 2411-2416.
Sannino, et al., "Development and Characterization of Cellulose-Based Hydrogels for Use as Dietary Bulking Agents", Journal of Applied Polymer Science, 115, 2010, 1438-1444.
Sannino, et al., "Introduction of Molecular Spacers Between the Crosslinks of a Cellulose-Based Superabsorbent Hydrogel: Effects on the Equilibrium Sorption Properties", Journal of Applied Polymer Science, 90, 2003, 168-174.
Sannino, et al., "Spin Coating Cellulose Derivatives on Quartz Crystal Microbalance Plates to Obtain Hydrogel-Based Fast Sensors and Actuators", Journal of Applied Polymer Sci., 106, 2007, 3040-3050.
Sannino, et al., "Water and Synthetic Urine Sorption Capacity of Cellulose-Based Hydrogels under a Compressive Stress Field", Journal of Applied Polymer Science, 91, 2004, 3791-3796.
Srokova, et al., "Water-Soluble Amphiphilic 0-(Carboxymethyl)-cellulose Derivatives—Synthesis and Properties", Macromolecular Materials Engineering 289, 2004, 63-69.
Xie, et al., "Development and Physicochemical Characterization of New Resistant Citrate Starch from Different Corn Starches", Starch, 56, 2004, 364-270.

METHOD FOR PRODUCING HYDROGELS COUPLING HIGH ELASTIC MODULUS AND ABSORBANCE

RELATED APPLICATIONS

This application is a continuation of U.S. application Ser. No. 15/010,626, filed on Jan. 29, 2016, which claims the benefit of U.S. Provisional Application No. 62/109,392, filed on Jan. 29, 2015. The entire teachings of the above applications are incorporated herein by reference.

BACKGROUND OF THE INVENTION

Polymer hydrogels are crosslinked hydrophilic polymers which are capable of absorbing and retaining large amounts of water. Certain of these materials are capable of absorbing over 1 kg of water per gram of dry polymer. The cross-links between the macromolecular chains form a network which guarantees the structural integrity of the polymer-liquid system and prevents the complete solubilisation of the polymer while allowing the retention of the aqueous phase within the molecular mesh. Polymer hydrogels having a particularly large capacity to retain water are referred to as superabsorbent polymer hydrogels (SAPs). High absorbency under load (AUL) is also a common characteristic of SAPs which in general is not displayed by polymer hydrogels having lower capacity to retain water. In addition to pressure, pH and other environmental conditions can affect the water retainment capacity of a polymer hydrogel, such as a SAP. Applications of highly absorbent polymer hydrogels include as absorbent cores in the field of absorbent personal hygiene products (Masuda, F., *Superabsorbent Polymers*, Ed. Japan Polymer Society, Kyoritsu Shuppann, (1987)) and as devices for the controlled release of water and nutrients into arid soils.

Carboxyalkyl cellulose materials and other carboxyalkyl polysaccharides are known in the art. Carboxyalkyl cellulose materials can be formed by treating a cellulosic material with a carboxyalkylating agent, such as a chloroalkanoic acid, usually monochloroacetic acid, and an alkali, such as sodium hydroxide, optionally in the presence of an alcohol. Such carboxyalkyl celluloses are generally water-soluble. Various methods of rendering such water-soluble carboxyalkyl celluloses water-insoluble are known. However, these methods rely on a stabilization mechanism which does not include the use of any cross-linker; the procedure involves selecting a proper range of temperature and heat treating time to transform the water soluble cellulose derivative into a non-water soluble form. The resulting stabilization appears to be mainly due to physical rather than chemical effects. In fact, at certain pH values, generally from about pH 10 and higher, the cellulose derivatives become water soluble again. (Flory, J. P. Principles of Polymer Chemistry; Cornell University: Ithaca, N.Y., 1953).

Other methods for the insolubilization of carboxyalkyl cellulose materials include the heat treatment of the carboxyalkyl cellulose in the presence of excess carboxyalkylating reactants and by-products of the carboxyalkylation reaction, to provide a water-insoluble carboxyalkyl cellulose having desirable liquid absorption and retention properties and characteristics. In these cases, the use of accelerators and catalysts to promote the stabilization (i.e., permanent cross-linking), coupled to a nonuniform distribution of the degree of cross-linking, result in an insoluble material having a low swelling capacity (Anbergen U., W. Opperman, Polymer, 31, 1854 (1990), Nijenhuis, K.te, *Advances in Polymer Science*, 130, (1997)).

Cellulose-based hydrogels can be obtained via either physical or chemical stabilization of aqueous solutions of cellulosics. Additional natural and/or synthetic polymers have been combined with cellulose to obtain composite hydrogels with specific properties [Chen, H.; Fan, M. Novel thermally sensitive pH-dependent chitosan/carboxymethylcellulose hydrogels. J. Bioact. Compat. Polym. 2008, 23 (1), 38-48. Chang, C.; Lue, A.; Zhang, L. Effects of cross-linking methods on structure and properties of cellulose/PVA hydrogels. Macromol. Chem. Phys., 2008, 209 (12), 1266-1273] (A. Sannino, M. Madaghiele, F. Conversano, A. Maffezzoli, P. A. Netti, L. Ambrosio and L. Nicolais' "Cellulose derivative-hyaluronic acid based microporous hydrogel cross-linked through divinyl sulfone (DVS) to modulate equilibrium sorption capacity and network stability", *Biomacromolecules*, Vol. 5, No. 1 (2004) 92-96). Physical, thermoreversible gels are usually prepared from water solutions of methylcellulose and/or hydroxypropyl methylcellulose (in a concentration of 1-10% by weight) [Sarkar, N. Thermal gelation properties of methyl and hydroxypropyl methylcellulose. J. Appl. Polym. Sci., 1979, 24 (4), 1073-1087]. The gelation mechanism involves hydrophobic associations among the macromolecules possessing the methoxy group. At low temperatures, polymer chains in solution are hydrated and simply entangled with one another. As temperature increases, macromolecules gradually lose their water of hydration, until polymer-polymer hydrophobic associations take place, thus forming the hydrogel network. The sol-gel transition temperature depends on the degree of substitution of the cellulose ethers as well as on the addition of salts. A higher degree of substitution of the cellulose derivatives provides them a more hydrophobic character, thus lowering the transition temperature at which hydrophobic associations take place. A similar effect is obtained by adding salts to the polymer solution, since salts reduce the hydration level of macromolecules by recalling the presence of water molecules around themselves. Both the degree of substitution and the salt concentration can be properly adjusted to obtain specific formulations gelling at 37° C. and are thus potentially useful for biomedical applications [Tate, M. C.; Shear, D. A.; Hoffman, S. W.; Stein, D. G.; LaPlaca, M. C. Biocompatibility of methylcellulose-based constructs designed for intracerebral gelation following experimental traumatic brain injury. Biomaterials, 2001, 22 (10), 1113-1123. Materials, 2009, 2, 370 Chen, C.; Tsai, C.; Chen, W.; Mi, F.; Liang, H.; Chen, S.; Sung, H. Novel living cell sheet harvest system composed of thermoreversible methylcellulose hydrogels. Biomacromolecules, 2006e7 (3), 736-743. Stabenfeldt, S. E.; Garcia, A. J.; LaPlaca, M. C. Thermoreversible laminin-functionalized hydrogel for neural tissue engineering. J. Biomed. Mater. Res., A 2006, 77 (4), 718-725.]. However, physically crosslinked hydrogels are reversible [Te Nijenhuis, K. On the nature of cross-links in thermoreversible gels. Polym. Bull., 2007, 58 (1), 27-42], and thus might flow under given conditions (e.g., mechanical loading) and might degrade in an uncontrollable manner. Due to such drawbacks, physical hydrogels based on methylcellulose and hydroxypropylmethylcellulose (HPMC) are not recommended for use in vivo.

As opposed to physical hydrogels which show flow properties, stable and stiff networks of cellulose can be prepared by inducing the formation of chemical, irreversible cross-links among the cellulose chains. Either chemical agents or physical treatments (i.e., high-energy radiation, thermal crosslinking) can be used to form stable cellulose-based networks. The degree of cross-linking, defined as the number of cross-linking sites per unit volume of the polymer network, affects the diffusive, mechanical and degradation properties of the hydrogel, in addition to the sorption thermodynamics, and can be controlled to a certain extent during the synthesis. Specific chemical modifications of the cellulose backbone might be performed before cross-linking, in order to obtain stable hydrogels with given properties. For instance, silylated HPMC has been developed which cross-links through condensation reactions upon a decrease of the pH in water solutions.

As a further example, tyramine-modified sodium carboxymethylcellulose (NaCMC) has been synthesized to obtain enzymatically gellable formulations for cell delivery [Ogushi, Y.; Sakai, S.; Kawakami, K. Synthesis of enzymatically-gellable carboxymethylcellulose for biomedical applications. J. Biosci. Bioeng., 2007, 104 (1), 30-33]. Photocrosslinking of aqueous solutions of cellulose derivatives is achievable following proper functionalization of cellulose. However, the use of chemical cross-linker and/or functionalizing agents provides a product which is not suitable for oral administration, especially in significant amounts and chronic use.

SUMMARY OF THE INVENTION

The present invention relates in part to the discovery that chemical cross-linking of high viscosity carboxymethylcellulose having a low polydispersity index results in the formation of crosslinked carboxymethylcellulose having significant absorption properties, rheological properties and other advantageous characteristics.

The present invention provides processes for producing crosslinked carboxymethylcellulose comprising cross-linking high viscosity carboxymethylcellulose. The invention further relates to the crosslinked carboxymethylcellulose produced using these processes. These cross-linked carboxymethylcelluloses have both a high elasticity modulus and high absorption capacity as described further herein. In fact, the cross-linked carboxymethycelluloses of the invention have significantly greater elasticity but similar absorption properties when compared to prior art crosslinked carboxymethylcelluloses. This is surprising in that an increase in elasticity is typically accompanied by a decrease in absorption properties (Flory J. P., "*Principles of Polymer Chemistry*", Cornell University Press, Ithaca N.Y., (1953); Peppas L. B. and Harland R. S. in "Absorbent Polymer Technology" Ed by L. B. Peppas, Elsevier Pub., Amsterdam (1990); F. L. Buchholz and N. A. Peppas Superabsorbent Polymers, Eds., ACS Symposium Series 573, Washington, D.C., 4, p.50 (1994)).

In one embodiment the invention provides a method of producing a crosslinked carboxymethylcellulose comprising the step of crosslinking a high viscosity carboxymethylcellulose with citric acid. The method further provides the crosslinked carboxymethylcelluloses produced by this method. Preferably, the high viscosity carboxymethylcellulose is crosslinked with an amount of citric acid from about 0.05% to about 0.5% by weight relative to the weight of the carboxymethylcellulose.

In one embodiment, the invention provides the method of producing a crosslinked carboxymethylcellulose comprises the steps of (1) preparing an aqueous solution of high viscosity carboxymethylcellulose and citric acid; (2) optionally agitating the solution, for example, by stirring; (3) isolating a carboxymethylcellulose/citric acid composite from the solution and (4) heating the carboxymethylcellulose/citric acid composite at a temperature of at least about 80° C., thereby cross-linking the carboxymethylcellulose with the citric acid. In one embodiment, the carboxymethylcellulose/citric acid composite is comminuted prior to conducting step (4). In one embodiment, the carboxymethylcellulose/citric acid composite is heated in step (4) to a temperature of about 80° C. or higher. The method further optionally includes the steps of (5) washing the crosslinked carboxymethylcellulose of step (4) and (6) comminuting the washed crosslinked carboxymethylcellulose.

The aqueous solution of carboxymethylcellulose and citric acid is preferably prepared by adding the carboxymethylcellulose and the citric acid to water and agitating, for example by stirring, the resulting mixture for a sufficient amount of time to create a homogenous solution.

The high viscosity carboxymethylcellulose is preferably present in the solution of step (1) in a concentration of at least about 1% by weight relative to water, preferably at least about 2%, 4% or 5%. In one embodiment, the concentration of the carboxymethylcellulose is about 6% by weight relative to water. In certain embodiments, the carboxymethylcellulose concentration is from about 2% to about 10%, about 4% to about 8%, from about 4.5% to about 7.5%, from about 5% to about 7%, or from about 5.5% to about 6.5% by weight relative to water.

The citric acid is preferably present in the solution of step (1) at a concentration of about 0.05% to about 0.5% by weight relative to the carboxymethylcellulose. More preferably, the citric acid is present in a concentration of about 0.1% to 0.5%; 0.4% or less; or 0.35% or less by weight relative to the carboxymethylcellulose. In an embodiment, the citric acid is present in the solution of step (1) in a concentration of about 0.15% to about 0.4%, about 0.15% to about 0.35%, 0.2% to about 0.35%, about 0.25% to about 0.35%, or about 0.2% by weight relative to the carboxymethylcellulose.

In one embodiment, the aqueous solution consists essentially of high viscosity carboxymethylcellulose, for example, as the sodium salt, citric acid and water. In a preferred embodiment, the solution consists essentially of high viscosity sodium carboxymethylcellulose, citric acid and water. The water is preferably purified water, such as distilled or deionized water. In this embodiment, the process is conducted in the substantial absence of any other agent that may affect the pH.

The cross-linking reaction is preferably conducted in the substantial absence of a catalyst.

In another embodiment, the invention provides a crosslinked carboxymethylcellulose produced by the methods disclosed herein. Such crosslinked carboxymethylcelluloses include citric acid crosslinked carboxymethylcelluloses having a high elastic modulus and a high media uptake ratio when determined as set forth herein. The crosslinked carboxymethylcellulose of this invention are additionally relatively insensitive to the high ionic strength of intestinal fluid. Coupling high sorption capacity to high elastic modulus is advantageous for a number of applications of these materials in therapies directed to the gastrointestinal tract, such as treatment of obesity and glycemic control. Without being bound by theory, a swollen hydrogel in the upper GI tract with elasticity better coupling the one of the ingested food would be expected to increase stomach emptying times and elastic response on stomach walls. Moreover, in the lower GI tract, higher elasticity of a swollen hydrogel may slow down the glucose trafficking, reducing glycemic peaks, in addition to generating a better bulk hindrance in the intestine. In the lower GI, partially digested food having high elasticity and bulk has been demonstrated to play a fundamental rule in metabolic pathways promoting weight loss (Saeidi N. et al., Science 2013, 341(6144):406-10). Thus, the crosslinked carboxymethylcellulose of the invention is expected to treat obesity and enhance glycemic control via multiple mechanisms.

In another embodiment, the invention provides methods of using the crosslinked carboxymethylcellulose of the invention, for example for reducing calorie intake, reducing weight or treating obesity in a subject in need thereof. The invention also provides methods of using the crosslinked carboxymethylcellulose of the invention in methods of enhancing glycemic control, treating diabetes or preventing diabetes in a subject in need thereof. Additional, the invention provides pharmaceutical compositions and articles of manufacture comprising a crosslinked carboxymethylcellulose of the invention.

DETAILED DESCRIPTION OF THE INVENTION

Figure 1:
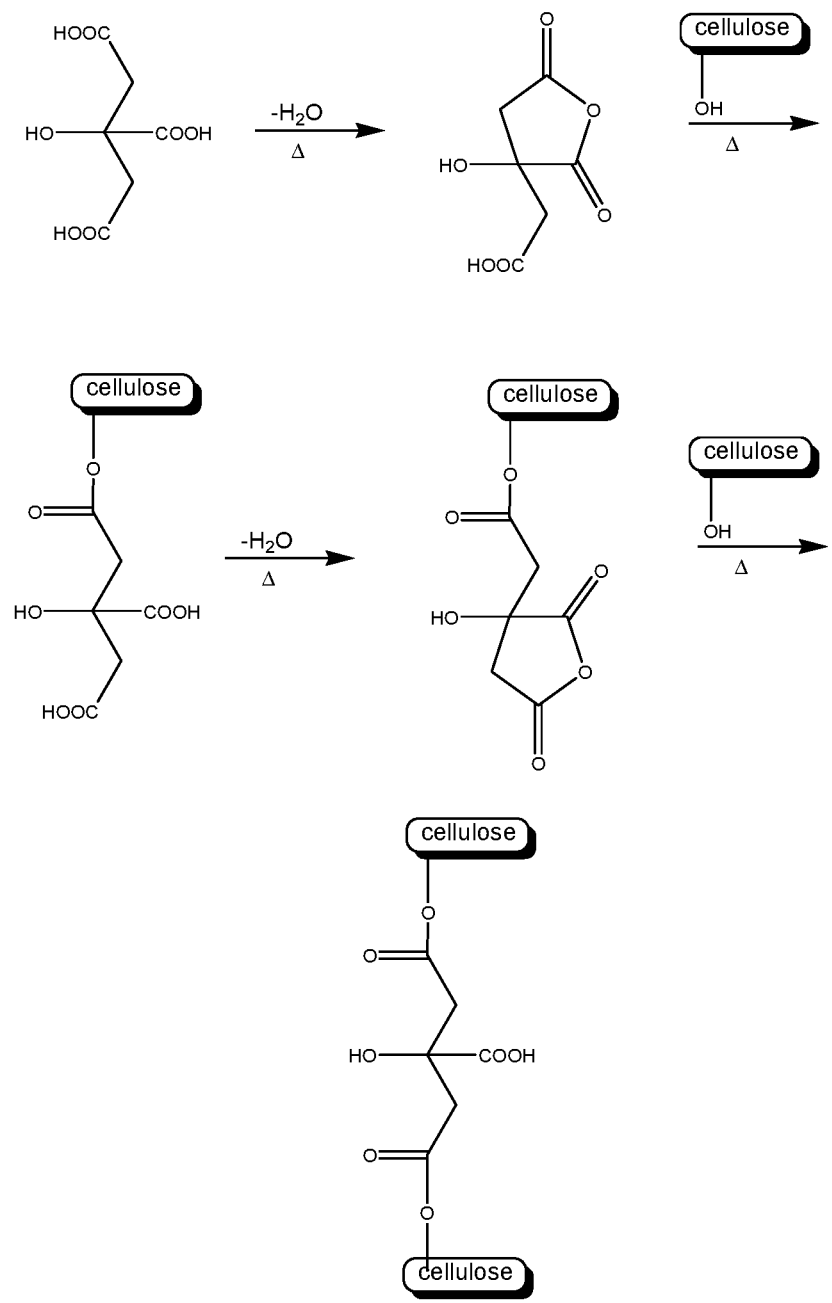
FIG. 1 illustrates the proposed mechanism of crosslinking of a cellulosic polymer by citric acid.

The present invention provides crosslinked carboxymethylcellulose, methods of producing the crosslinked carboxymethylcellulose, methods of use of the crosslinked carboxymethylcellulose and articles of manufacture comprising the crosslinked carboxymethylcellulose. In certain embodiments, the invention relates to the discovery that chemically crosslinking high viscosity carboxymethylcellulose provides crosslinked carboxymethylcellulose having advantageous properties.

The high viscosity carboxymethylcellulose can be chemically crosslinked using a suitable polyfunctional, for example, bifunctional, crosslinking agent which produces covalent crosslinks. Suitable crosslinking agents include polycarboxylic acids, such as oxalic acid or citric acid, divinylsulphone (DVS), aldehydes, such as acetaldehyde, formaldehyde and glutaraldehyde, diglycidyl ether, diisocyanates, dimethyl urea, epichlorohydrin, oxalic acid, phosphoryl chloride, trimetaphosphate, trimethylomelamine, and polyacrolein. The carboxymethylcellulose can also be crosslinked to itself, without the presence of the crosslinking agent in the product. For example carboxymethylcelulose can be crosslinked in the presence of a carboxy activating agent, such as a carbodiimide, or by heat treatment. It is also possible to ionically crosslink or physically crosslink the carboxymethylcellulose.

Preferably, the high viscosity carboxymethylcellulose is crosslinked with citric acid.

In one embodiment, the method of producing a crosslinked carboxymethylcellulose comprises the steps of: (1) preparing an aqueous solution of high viscosity carboxymethylcellulose and citric acid; (2) optionally agitating the solution; (3) isolating a carboxymethylcellulose/citric acid composite from the solution; and (4) heating the carboxymethylcellulose/citric acid composite at a temperature of at least about 80° C., thereby producing the crosslinked carboxymethylcellulose. In one embodiment, the carboxymethylcellulose/citric acid composite is comminuted prior to conducting step (4) and optionally sieved to obtain particles of a desired size range. In one embodiment, the crosslinked carboxymethylcellulose product of step (4) is washed and comminuted, for example, by grinding or milling, and optionally sieved. In certain embodiments, the carboxymethylcellulose/citric acid composite is comminuted prior to conducting step (4) and optionally sieved to obtain particles of a desired size range; and the crosslinked carboxymethylcellulose product of step (4) is comminuted to produce crosslinked carboxymethylcellulose particles, and the particles are optionally sieved.

The carboxymethylcellulose is preferably present in the solution of step (1) in a concentration of at least about 1% by weight relative to water, preferably at least about 2%, 4% or 5%. In one embodiment, the concentration of the carboxymethylcellulose is about 6% by weight relative to water. In certain embodiments, the carboxymethylcellulose concentration is from about 2% to about 10%, about 4% to about 8%, from about 4.5% to about 7.5%, from about 5% to about 7%, or from about 5.5% to about 6.5% by weight relative to water.

The citric acid is preferably present in the solution of step (1) at a concentration of about 0.05% to about 0.5% by weight relative to the carboxymethylcellulose. Preferably, the citric acid is present in a concentration of about 0.4% or less or 0.35% or less by weight relative to the carboxymethylcellulose. In an embodiment, the citric acid is present in the solution of step (1) in a concentration of about 0.1% to about 0.5%, 0.15% to about 0.4%, about 0.15% to about 0.35%, 0.2% to about 0.35%, about 0.25% to about 0.35%, or about 0.2% by weight relative to the carboxymethylcellulose.

In the methods of the invention, the carboxymethylcellulose/citric acid composite can be isolated from the solution by any method that avoids substantial deterioration of the absorption characteristics of the resulting crosslinked carboxymethylcellulose. Examples of such methods include evaporative drying, freeze drying, precipitation, centrifugation, spray drying, critical point drying, and the like.

In the methods of the invention, the carboxymethylcellulose/citric acid composite is preferably isolated by evaporative drying at a temperature within the range from about 10° C. to about 100° C., preferably from about 45° C. to about 80° C. In certain embodiments, drying is conducted at an initial temperature of about 80° C. or higher, for example, from 80° C. to 100° C., to substantially reduce the solution volume, then the temperature is reduced below 80° C. to complete the drying. For example, the solution can be dried initially at 85° C., and then the temperature can be reduced to 50° C. to complete the drying. Naturally, higher temperatures can be employed if the solution is placed under pressure. Lower temperatures can be employed if the solution is placed under a vacuum. In one preferred embodiment, evaporative drying is conducted at a temperature of about 65 to 75° C. or about 70° C.

In embodiments of the methods of the invention in which the solution is dried by heating, the step of isolating the carboxymethylcellulose/citric acid composite and the step of crosslinking the composite can be combined in a single step, preferably with a temperature change.

Other methods of isolation of the composite which can be sued in the methods of the invention include precipitation in which a precipitating agent (non-solvent), such as methanol, ethanol or acetone is added to the aqueous solution to precipitate the composite from solution. The composite can then be recovered by filtration. If precipitation is used to recover the composite, the composite is optionally washed with water to remove the precipitating agent.

If evaporative drying by spray drying is employed, the composite may be recovered in the form of particles, flakes or granules prior to the cross-linking step.

In one embodiment, the method of the invention includes the steps of (1) preparing an aqueous solution of high viscosity carboxymethylcellulose and citric acid; (2) agitating the solution; (3) heating the solution to remove water and produce a carboxymethylcellulose/citric acid composite; (3a) comminuting the carboxymethylcellulose/citric acid composite to produce composite particles; (4) heating the composite particles at a temperature of at least about 80° C., thereby cross-linking the carboxymethylcellulose with the citric acid and forming the crosslinked carboxymethylcellulose; (5) washing the crosslinked carboxymethylcellulose; (6) drying the washed crosslinked carboxymethylcellulose and, optionally, (7) comminuting the crosslinked carboxymethylcellulose to produce crosslinked carboxymethylcellulose particles. The particles produced in either or both of steps (3a) and (7) can be sieved to yield a sample of particles within a specified size range.

One preferred embodiment of the method of the invention comprises the following steps: (1), high viscosity sodium carboxymethylcellulose and citric acid are dissolved in purified water to produce a solution essentially consisting of about 5% to about 7%, preferably about 6%, sodium carboxymethylcellulose by weight relative to the weight of water, and citric acid in an amount of about 0.15% to about 0.40%, about 0.15% to about 0.35%, about 0.15% to 0.25% or about 0.2% by weight relative to the weight of sodium carboxymethylcellulose; (2), maintaining the solution at a temperature from about 40° C. to about 70° C. or 40° C. to about 80° C., preferably about 70° C., to evaporate the water and form a carboxymethylcellulose/citric acid composite; (3), comminuting the carboxymethylcellulose/citric acid composite to form composite particles; and (4), maintaining the composite particles at a temperature from about 80° C. to about 150° C. or about 100° C. to about 150° C., about 115° C. to about 125° C. preferably, about 120° C., for a period of time sufficient to achieve the desired degree of cross-linking and form the crosslinked carboxymethylcellulose. The method can optionally further include one or more of Step (5), washing the crosslinked carboxymethylcellulose with purified water, preferably with an amount of purified water from 100 to 200 times the mass of the crosslinked carboxymethylcellulose, preferably about 150 times the mass of the crosslinked carboxymethylcellulose; Step (6), drying the washed crosslinked carboxymethylcellulose at elevated temperature, preferably from about 40° C. to about 70° C. or 40° C. to about 80° C., more preferably about 70° C.; and Step (7), comminuting the dried crosslinked carboxymethylcellulose. In one embodiment, the resulting particles are sieved to the size range of 100 μm to 1000 μm, preferably with an average size in the range of 400 to 800 μm.

In another particularly preferred embodiment, the method for preparing a crosslinked carboxymethylcellulose of the invention comprises the steps of (a) providing an aqueous solution consisting essentially of: (a) high viscosity sodium carboxymethylcellulose, citric acid and water; (b) stirring the aqueous solution; (c) evaporating the water, for example by maintaining the solution at a temperature from about 40° C. to about 70° C. or 40° C. to about 80° C., preferably about 70° C., to form a carboxymethylcellulose/citric acid composite; (d) comminuting the composite to form composite particles; and (e) heating the composite particles to a temperature of at least about 80° C. or 100° C. for example from 100° C. to 180° C., from 100° C. to 150° C., from 110° C. to 130° C., from about 115° C. to about 125° C. or about 120° C., thereby cross-linking the carboxymethylcellulose and forming a citric acid crosslinked carboxymethylcellulose.

The product of step (e) is optionally comminuted to produce particles which are optionally sieved. In other embodiments, the product of step (e) is washed, dried and then comminuted to produce particles which are optionally sieved. In one embodiment, the crosslinked carboxymethylcellulose consists substantially of particles in the size range from 1 μm to 2000 μm, preferably from 10 μm to 2000 μm, and more preferably from 100 μm to 1000 μm. A sample of crosslinked carboxymethylcellulose consists substantially of particles in a specified size range when the sample is greater than 50% by mass particles in the specified size range. Preferably, the sample is at least 50%, 60%, 70%, 80%, 90% or 95% by mass particles in the specified size range. More preferably the sample is at least 90 or 95% by mass particles in the size range of 100 μm to 1000 μm, preferably with an average particle diameter in the range of 400 μm to 800 μm.

The high viscosity sodium carboxymethylcellulose is preferably present in the aqueous solution of step (a) at a concentration of 4% or greater, preferably from about 4% to about 8%, 5% to about 7%, 5.5% to about 6.5% or about 6% by weight relative to the weight of the water used to prepare the solution. Preferably the citric acid is present in the solution at a concentration of about 0.5% or less, more preferably, about 0.35% or less or about 0.3% or less by weight relative to the weight of the cellulose derivative. Preferably the concentration of the citric acid is about 0.15% to about 0.35%, preferably about 0.2% to about 0.35%, 0.15% to about 0.3%, 0.15 to 0.25% or about 0.2% by weight relative to the sodium carboxymethylcellulose. sodium salt.

In any embodiment of the methods of the invention, the high viscosity carboxymethylcellulose is preferably present in the aqueous solution in a concentration of about 5 to about 7%, preferably about 6 wt% relative to the weight of the water, and the citric acid is present at a concentration of 0.1 to 0.4%, preferably 0.15 to 0.3% by weight relative to the weight of the carboxymethylcellulose.

In certain embodiments of the methods of the invention, the aqueous solution is dried to form the composite as a sheet, which is comminuted to form composite particles. Preferably the composite particles have a greatest dimension between about 10 μm and about 2000 μm, more preferably between about 100 μm and about 2000 μm, or between about 100 μm and about 1600 μm with an average size of between 300 μm and 600 μm. The composite particles are optionally sieved to provide particles in the desired size range.

In preferred embodiments of the methods of the invention, the aqueous solution is placed in a tray prior to removing the water. The heating preferably is conducted in a suitable oven or vacuum oven.

In the methods of the invention, the composite can be comminuted, for example, by grinding, milling or fragmenting, to form composite particles, and the particles are maintained at elevated temperature, thereby effecting cross-linking and producing crosslinked carboxymethylcellulose particles.

The methods of the invention can further include the step of washing the crosslinked carboxymethylcellulose, for example, washing the crosslinked carboxymethylcellulose in a polar solvent, such as water, a polar organic solvent, for example, an alcohol, such as methanol or ethanol, or a combination thereof.

In preferred embodiments of the methods of the invention, the crosslinked carboxymethylcellulose is washed with an amount of purified water which is 50 to 250-fold greater (wt/wt) than the amount of the crosslinked polymer. In certain embodiments, the amount of purified water is 100 to 200-fold greater (wt/wt) than the amount of the crosslinked polymer. In certain embodiments, the amount of purified water is about 150-fold greater (wt/wt) than the amount of the crosslinked polymer.

The washed crosslinked carboxymethylcellulose can further be dried to remove most or substantially all water. Preferably the crosslinked carboxymethylcellulose is dried to a water content of about 25% by weight or less, preferably about 20%, about 15% or about 10% or less. In certain embodiments, the water content of the dried crosslinked carboxymethylcellulose is about 5% or less by weight.

In one embodiment, the drying step is carried out by immersing the fully swollen crosslinked carboxymethylcellulose in a cellulose non-solvent, a process known as phase inversion. A "cellulose non-solvent", as this term is used herein, is a liquid compound which does not dissolve carboxymethylcellulose and does not swell the crosslinked carboxymethylcellulose, but is preferably miscible with water. Suitable cellulose non-solvents include, for example, acetone, methanol, ethanol, isopropanol and toluene. Following immersion in the nonsolvent, residual nonsovent can be removed from crosslinked carboxymethylcellulose by vacuum and/or heating.

In other embodiments, the crosslinked carboxymethylcellulose is not dried by phase inversion. The washed crosslinked carboxymethylcellulose is preferably dried by air drying, vacuum drying, freeze drying or by drying at elevated temperature, for example, in an oven or vacuum oven. These drying methods can be used alone or in combination. Oven drying can be carried out at a temperature of, for example, approximately 30-80° C. until the water or residual non-solvent is completely removed. The washed and dried crosslinked carboxymethylcellulose can then be used as is, or can be comminuted and optionally sieved to produce crosslinked carboxymethylcellulose particles of a desired size.

In the methods of the invention, the aqueous solution of the carboxymethylcellulose and the citric acid can be formed at any temperature at which the carboxymethylcellulose derivative is soluble in the water. Generally, such temperatures will be within the range of from about 10° C. to about 100° C. Preferably, the solution is prepared substantially at room temperature, for example, between 20° C. and 30° C. or about 25° C.

In any embodiment of the methods of the invention it is preferred to have the pH of the aqueous solution of high viscosity carboxymethylcellulose and citric acid between about 5 to about 9, from about 5 to about 8, from about 6 to 8, from about 6 to about 7, from about 6.5 to about 7.5 or about 5.5 to about 7. More preferably the solution pH is between 6 and 7.

Without being bound by theory, is believed that the carboxymethylcellulose/citric acid composite isolated from the aqueous solution is suitable for chemical cross-linking to form crosslinked carboxymethylcellulose having improved absorption properties due to the inter-chain entanglements. Without being bound by theory, it is believed that solubilization provides for molecular entanglements which produce a tighter network and a preferred distribution of the carboxyl groups and hydroxyl groups between the carboxymethylcellulose and the citric acid. Greater entanglement of the carboxymethylcellulose chains thus results in a more uniform cross-linking upon heat-treatment, resulting, in turn in a super-absorbent crosslinked carboxymethylcellulose with a greater media uptake capacity and significantly improved mechanical and rheological properties.

In methods of the invention comprising the step of comminuting the carboxymethylcellulose/citric acid composite, the resulting composite particles preferably have a maximum cross-sectional diameter or greatest dimension within the range from about 5 μm to about 2,000 μm, preferably within the range from about 100 μm to about 1,000 μm, and more preferably the average particle cross-sectional diameter is from about 300 μm to about 800 μm.

Without being bound by theory, it is believed that the step of comminuting the composite prior to crosslinking provides a homogeneous distribution of cross-linking sites as well as enhanced water evaporation before the crosslinking reaction begins, resulting in a material with high conservative modulus (G') and uniform chemical stabilization and increasing the extent of the reaction.

In the methods of the invention, the isolated carboxymethylcellulose/citric acid composite or particles thereof are preferably heated to a temperature of at least about 80° C. to cross-link the carboxymethylcellulose. Any combination of temperature and time which achieves a desired degree of cross-linking, without undesirable damage to the carboxymethylcellulose, is suitable for use in the present invention. Preferably the composite is heated to a temperature of 80° C. or greater, for example, 100° C. or greater. In certain embodiments, the temperature is within the range from about 100° C. to about 250° C., preferably from about 100° C. to about 200° C., and more preferably from about 110° C. to about 150° C. In a particularly preferred embodiment, the composite is heated to 110 to 130° C. or to about 120° C. Generally, the heat-treating process will extend over a time period within the range of from about 1 minute to about 600 minutes, preferably from about 1 minute to about 300 minutes, and more preferably from about 175 minutes to about 300 minutes, or about 200 to 250 minutes. In preferred embodiments, the composite is crosslinked by heating at about 120° C. for 200 to 250 minutes or about 225 minutes.

The heat treatment of the carboxymethylcellulose/citric acid composite in the methods of the invention causes the carboxymethylcellulose chains to cross-link via the citric acid and become water-insoluble. The heat-treating process desirably produces a citric acid crosslinked carboxymethylcellulose having an elastic modulus and the ability to absorb aqueous liquids, in particular stomach fluids which have high salinity and low pH.

The term "carboxymethylcellulose/citric acid composite" or "composite" as used herein, refers to a substantially dry material comprising a mixture of the carboxymethylcellulose and the citric acid. In embodiments in which this composite is produced by evaporative drying of the aqueous solution of high viscosity carboxymethylcellulose and citric acid, the composite is the substantially dry residue which remains following removal of water. The composite can retain some bound water, and can be, for example, up to 5, 10 or 20% water by weight. Preferably the composite is about 10% water by weight or less.

Without being bound by theory, it is believed that the preparation of crosslinked carboxymethylcellulose as disclosed herein proceeds via covalent cross-linking of the carboxymethylcellulose with citric acid. FIG. 1 illustrates the cross-linking of a soluble cellulose derivative, such as carboxymethylcellulose, with citric acid. In this mechanism, the C1-carboxyl group of citric acid is activated by anhydride formation at neutral pH and at elevated temperature and in the presence of a very small amount of water, and in the absence of catalyst reacts with a cellulosic hydroxyl group to form an ester. The C5 carboxyl group is then activated by anhydride formation and reacts with a hydroxyl group of another cellulosic polymer chain to form an intermolecular covalent crosslink, or the same chain to form an intramolecular covalent crosslink. Because this is an equilibrium reaction with water as a product, the more water that is eliminated during the stabilization procedure, the higher the degree of conversion that may be achieved. Removal of water from the carboxymethylcellulose/citric acid solution to form a carboxymethylcellulose/citric acid composite before crosslinking is thus necessary to allow the anhydride formation/esterification reaction to occur.

The term "carboxymethylcellulose" (CMC), as used herein, refers to carboxymethylcellulose (cellulose carboxymethyl ether) in the acid form, as a salt or as a combination of the acid form and a salt. Preferred salt forms include sodium carboxymethylcellulose and potassium carboxymethylcellulose. In particularly preferred embodiments, the carboxymethylcellulose is present in the solution as the sodium salt (NaCMC).

Methods of making carboxymethylcellulose are known to those skilled in the art. Suitably, a cellulosic material such as cotton or wood pulp is provided. The cellulosic material may be in the form of fibers or fibers which have been comminuted to particulate form. The cellulosic material is dispersed in an inert solvent such as an alcohol and a carboxyalkylating agent is added to the dispersion. Carboxyalkylating agents generally comprise a chloroalkanoic acid such as monochloroacetic acid and sodium hydroxide. It is possible to perform the carboxymethylation of the starting cellulose in such a manner that the solution of carboxymethylcellulose and water is formed directly. That is, the carboxymethylation process may be performed in an aqueous medium such that, upon formation of the carboxymethyl cellulose, it is solubilized in the water. In this manner, no recovery step is necessary between formation of the carboxymethylcellulose and the formation of the solution of carboxymethylcellulose and water.

In certain embodiments, the high-viscosity carboxymethylcellulose is prepared from cellulose from cotton. In other embodiments, the high-viscosity carboxymethylcellulose is prepared from cellulose from both cotton and wood pulp.

The term "high viscosity carboxymethylcellulose", as used herein, refers to carboxymethylcellulose, typically as the sodium salt, which forms a 1% (wt/wt) solution in water having a viscosity of at least 6000 cps. The viscosity is determined according to the method set forth in Example 5 which is in accordance with ASTM D1439-03(2008)e1 (ASTM International, West Conshohocken, Pa. (2008), incorporated herein by reference in its entirety). In preferred ambidoments, the high viscosity carboxymethylcellulose also has a low polydispersity index, such as a polydispersity index of about 8 or less.

In any embodiment of the invention, the high viscosity carboxymethylcellulose preferably forms a 1% (wt/wt) solution in water having a viscosity at 25° C. of at least about 6000, 7000, 7500, or 8000 cps. In certain embodiments, the carboxymethylcellulose forms a 1% (wt/wt) aqueous solution having a viscosity of 6000 to about 10000 cps or about 6000 to 11000 cps at 25° C. In certain embodiment, the carboxymethylcellulose forms a 1% (wt/wt) aqueous solution having a viscosity of about 6000 to about 9500 cps or about 7000 to 9500 cps at 25° C. In another embodiment, the carboxymethylcellulose forms a 1% (wt/wt) aqueous solution having a viscosity of about 7000 to about 9200 cps or about 7500 to 9000 cps at 25° C. In yet another embodiment, the carboxymethylcellulose forms a 1% (wt/wt) aqueous solution having a viscosity of about 8000 to about 9300 cps, or about 9000 cps at 25° C. Preferably the carboxymethylcellulose is in the form of the sodium salt. In preferred embodiments the carboxymethylcellulose is sodium carboxymethylcellulose which forms a 1% (wt/wt) aqueous solution having a viscosity of about 7800 cps or higher, for example, from about 7800 to 11000 cps, or about 8000 cps to about 11000 cps. In preferred embodiments, the high viscosity carboxymethylcellulose further has a polydispersity index (Mw/Mn) of about 8 or less, preferably about 7 or less, or 6 or less. In one embodiment, the polydispersity index is from about 3 to about 8, about 3 to about 7, about 3 to about 6.5, about 3.0 to about 6; about 3.5 to about 8, about 3.5 to about 7, about 3.5 to about 6.5, about 3.5 to about 6, about 4 to about 8, about 4 to about 7, about 4 to about 6.5, about 4 to about 6, about 4.5 to about 8, about 4.5 to about 7, about 4.5 to about 6.5, about 4.5 to about 6, about 5 to about 8, about 5 to about 7.5, about 5 to about 7, about 5 to about 6.5, or about 5 to about 6.

As used herein, the term "polydispersity index" in relation to a carboxymethylcellulose refers to the polydispersity index determined using the procedure set forth in Example 10.

The high viscosity carboxymethylcellulose or salt thereof preferably has an average degree of substitution from about 0.3 to about 1.5, more preferably from about 0.4 to about 1.2. In particularly preferred embodiments, the high viscosity carboxymethylcelllulose has a degree of substitution from about 0.60 to about 0.95, 0.65 to 0.95, 0.65 to 0.90, 0.70 to 0.80, 0.72 to 0.78 or 0.73 to 0.75. The degree of substitution refers to the average number of carboxyl groups present on the anhydroglucose unit of the cellulosic material. Carboxymethylcelluloses having an average degree of substitution within the range of from about 0.3 to about 1.5 are generally water-soluble. As used herein, a carboxymethylcellulose is considered to be "water-soluble" when it dissolves in water to form a true solution.

In certain embodiments, the high viscosity carboxymethylcellulose is sodium carboxymethylcellulose which forms a 1% (wt/wt) aqueous solution having a viscosity of about 7600 cps or higher, for example, from about 7800 to 15000 cps, about 7800 to about 11000 cps, about 8000 to about 15000 cps or about 8000 cps to about 11000 cps, and has a polydispersity index of about 3 to about 8, about 3 to about 7, about 3 to about 6.5, about 3 to about 6; about 3.5 to about 8, about 3.5 to about 7, about 3.5 to about 6.5, about 3.5 to about 6, about 4 to about 8, about 4 to about 7, about 4 to about 6.5, about 4 to about 6, about 4.5 to about 8, about 4.5 to about 7, about 4.5 to about 6.5, about 4.5 to about 6, about 5 to about 8, about 5 to about 7.5, about 5 to about 7, about 5 to about 6.5, or about 5 to about 6. In certain embodiments, the high viscosity sodium carboxymethylcellulose additionally has a degree of substitution of 0.65 to 0.90, 0.70 to 0.80, 0.72 to 0.78 or 0.73 to 0.75.

In particularly preferred embodiments, the high viscosity sodium carboxymethylcellulose forms a 1% (wt/wt) aqueous solution having a viscosity at 25° C. of about about 8000 cps to about 11000 cps, has a degree of substitution of 0.65 to 0.90 or 0.70 to 0.80 and a polydispersity of about 4.5 to about 6.5.

In certain embodiments the high viscosity carboxymethylcellulose has a weight average molecular weight (Mw) of at least 2800 kDa when determined as described in Example 10. Preferably the Mw is at least about 2900 kDa, or at least about 3000 kDa, or from about 2800 kDa to about 3500 kDa.

The carboxymethylcellulose and the citric acid used in the methods of the invention are preferably are each food grade or pharmaceutical grade materials. For example, carboxymethylcellulose and citric acid are both used as food additives and pharmaceutical excipients and are, therefore, available in forms which are suitable for these uses.

A suitable carboxymethylcellulose sodium salt for use in the processes of the invention is AQUALON™ 7H4FM sold by Ashland Inc.

The present invention further provides crosslinked carboxymethylcelluloses, including superabsorbent crosslinked carboxymethylcelluloses, which can be prepared by crosslinking high viscosity carboxymethylcellulose with citric acid, for example, using the methods of the invention, also referred to herein as "citric acid crosslinked carboxymethylcelluloses". The invention includes articles of manufacture, pharmaceutical compositions, foods, foodstuffs and medical devices, agriculture and horticulture products, personal hygiene products which comprise such crosslinked carboxymethylcelluloses. The invention further includes methods of use of the crosslinked carboxymethylcelluloses of the invention for the preparation of foods, the treatment of obesity and diabetes and the enhancement of glycemic control.

In certain embodiments, citric acid crosslinked carboxymethylcelluloses produced by the methods described herein form hydrogels that have greater elastic modulus than carboxymethylcellulose hydrogels produced using other methods, while retaining significant absorption properties. In preferred embodiments, the citric acid crosslinked carboxymethylcellulose of the invention has a G' and an MUR as set forth below. In more preferred embodiments, the citric acid crosslinked carboxymethycellulose additionally has a tapped density as set forth below.

The methods of the invention produce citric acid crosslinked carboxymethylcelluloses which combine both physical and chemical cross-linking and which have good mechanical properties, long term stability in dry and swollen form and good retention capacity and biocompatibility. The crosslinked carboxymethylcelluloses of the invention exhibit good media uptake properties, high tapped density, high elastic modulus and cost effective production. Further, the crosslinked carboxymethylcelluloses have rapid media uptake kinetics in body fluids.

In any embodiment, the citric acid crosslinked carboxymethylcelluloses of the invention preferably have a media uptake ratio in distilled water of at least about 20, about 30, about 40, about 50, about 60, about 70, about 80, about 90 or about 100. For example, in certain embodiments, the citric acid crosslinked carboxymethylcelluloses of the invention have a media uptake ratio in distilled water from about 20 to about 1000, from about 35 to about 750, from about 50 to about 500, from about 50 to about 250, from about 50 to about 150. In certain embodiments, the citric acid crosslinked carboxymethylcelluloses of the invention have a media uptake ratio in distilled water from about 20, 30, 40, 50, 60, 70, 80, 90 or 100 to about 120, 150, 200, 300, 400, 500, 600, 700, 800, 900, 1000 or greater, or within any range bounded by any one of these lower limits and any one of these upper limits.

In certain embodiments, the citric acid crosslinked carboxymethylcelluloses of the invention can absorb an amount of one or more bodily fluids, such as blood, blood plasma, urine, intestinal fluid or gastric fluid, which is at least 10, 20, 30, 40, 50, 60, 70, 80, 90, or 100 times their dry weight. The ability of the citric acid crosslinked carboxymethylcellulose to absorb bodily fluids can be tested using conventional means, including testing with samples of bodily fluids obtained from one or more subjects or with simulated bodily fluids, such as simulated urine or gastric fluid.

In any embodiment embodiments, the citric acid crosslinked carboxymethylcellulose of the invention can preferably absorb significant amounts of SGF/water (1:8). In some embodiments, the citric acid crosslinked carboxymethylcelluloses of the invention have a media uptake ratio of at least 10, 20, 30, 40, 50, 60, 70, 80, 90, 100, or 150 in SGF/water (1:8). In some embodiments the citric acid crosslinked carboxymethylcelluloses of the invention have a media uptake ratio of 10 to 300, from 20 to 250, from 30 to 200, from 50 to 180, from 50 to 150, from 50 to 100 or from 50 to 80 in SGF/water (1:8). In preferred embodiments the citric acid crosslinked carboxymethylcellulose has a media uptake ratio of about 40 or greater or 50 or greater in SGF/water (1:8), for example from about 50 to about 110, about 55 to about 100, about 60 to about 95, about 60 to about 90, about 60 to about 85, about 50 to about 120, about 60 to about 100 or about 70 to about 100.

Preferably, the citric acid crosslinked carboxymethylcellulose of the invention has a G' when swollen in SGF/water (1:8) of at least 1500 Pa, 2000 Pa, 2200 Pa, 2500 Pa, or 2700 Pa as determined according to the method described in Example 5. In certain embodiments, the citric acid crosslinked carboxymethylcellulose of the invention has a G' when swollen in SGF/water (1:8) of at least about 2800 Pa. In certain embodiments, the citric acid crosslinked carboxymethylcellulose of the invention has a G' when swollen in SGF/water (1:8) from about 1800 Pa to about 4000 Pa, from about 2000 Pa to about 3500 Pa, from about 2100 Pa to about 3400 Pa or from about 2500 Pa to about 3500 Pa.

The citric acid crosslinked carboxymethylcelluloses of the invention are preferably glassy but amorphous or vitreous materials when in a substantially dry or xerogel form. The citric acid crosslinked carboxymethylcellulose of the invention preferably has a tapped density of at least about 0.45 g/mL. In more preferred embodiments, the tapped density is from about 0.50 to about 0.8 g/mL or from about 0.55 to about 0.8 g/mL when determined as described in Example 5. In a preferred embodiment, the tapped density is about 0.6 g/mL or greater, for example, from about 0.6 g/mL to about 0.8 g/mL. In certain embodiments, the tapped density is from about 0.65 g/mL to about 0.75 g/mL.

The citric acid crosslinked carboxymethylcelluloses of the invention include crosslinked polymers having varying extents of hydration. For example, the citric acid crosslinked carboxymethylcelluloses can be provided in a state of hydration ranging from a substantially dry or anhydrous state, such as a xerogel or a state in which from about 0% to about 5% or up to about 10% of the citric acid crosslinked carboxymethylcellulose by weight is water or an aqueous fluid, to states comprising a substantial amount of water or aqueous fluid, including up to a state in which the citric acid crosslinked carboxymethylcellulose has absorbed a maximum amount of water or an aqueous fluid. In certain embodiments, the citric acid crosslinked carboxymethylcellulose has a water content of 25% or less, 20% or less, 15% or less, 10% or less or 5% or less by weight. Preferably the citric acid crosslinked carboxymethylcellulose has a water content of less than about 10% by weight, more preferably about 6% or less or about 5% or less, when determined according to the method of Example 5.

In certain embodiments, the invention provides a citric acid crosslinked carboxymethylcellulose which, when in the form of particles which are at least 95% by mass in the range of 100 μm to 1000 μm with an average size in the range of 400 to 800 μm and a loss on drying of 10% or less (wt/wt), has a G', media uptake ratio, and tapped density as described below. Such a crosslinked carboxymethylcellulose can be prepared, for example, according to the methods disclosed herein.

(A) G': at least about 1500 Pa, 1800Pa, 2000 Pa, 2200 Pa, 2500 Pa, or 2700 Pa. In certain embodiments, the crosslinked carboxymethylcellulose of the invention has a G' when swollen in SGF/water (1:8) of at least about 2800 Pa. In certain embodiments, the crosslinked carboxymethylcellulose of the invention has a G' when swollen in SGF/water (1:8) from about 1800 Pa to about 3000 Pa, about 2000 Pa to about 4000 Pa, from about 2100 Pa to about 3500 Pa, from about 2100 Pa to about 3400 Pa, or from about 2500 Pa to about 3500 Pa.

(B) Media uptake ratio (MUR) in SGF/water (1:8): at least about 50, preferably at least about 60. In certain embodiments, the crosslinked carboxymethylcellulose has an MUR of about 50 to about 110, about 55 to about 100, about 60 to about 95, about 60 to about 90, or about 60 to about 85.

(C) Tapped density: at least 0.5 g/mL, preferably about 0.55 g/mL to about 0.9 g/mL. In a preferred embodiment, the tapped density is about 0.6 g/mL or greater, for example, from about 0.6 g/mL to about 0.8 g/mL, about 6.5 g/mL to about 7.5 g/mL or about 0.6 g/mL to about 0.7 g/mL.

In certain embodiments, the invention provides a citric acid crosslinked carboxymethylcellulose which has a G' and media uptake ratio as set forth below when in the form of particles which are at least 95% by mass in the range of 100 μm to 1000 μm with an average size in the range of 400 to 800 μm and a loss on drying of 10% or less (wt/wt):

(A) G' of about 1200 Pa to about 2000 Pa and a media uptake ratio of at least about 90;
(B) G' of about 1400 Pa to about 2500 Pa and a media uptake ratio of about 80 to 89;
(C) G' of about 1600 Pa to about 3000 Pa and a media uptake ratio of about 70 to 79;
(D) G' of about 1900 Pa to about 3500 Pa and a media uptake ratio of about 60 to 69;
(E) G' of about 2200 Pa to about 4000 Pa and a media uptake ratio of about 50 to 59; or
(F) G' of about 2600 Pa to about 5000 Pa and a media uptake ratio of about 40 to 49.

In these embodiments, the citric acid crosslinked carboxymethylcellulose optionally further has a tapped density of at least 0.5 g/mL, preferably about 0.55 g/mL to about 0.9 g/mL. In a preferred embodiment, the tapped density is about 0.6 g/mL or greater, for example, from about 0.6 g/mL to about 0.8 g/mL, about 6.5g/mL to about 7.5 g/mL or about 0.6 g/mL to about 0.7 g/mL.

In exemplary but non-limiting embodiments, the citric acid crosslinked carboxymethylcellulose has a G' of at least about 2100 Pa and a media uptake ratio of at least about 80; or a G' of at least about 2700 Pa and a media uptake ratio of at least about 70.

Unless otherwise noted, all measurements of G', MUR and tapped density described herein are made on samples of citric acid crosslinked carboxymethylcellulose having (1) a loss on drying of 10% (wt/wt) or less; and (2) are in the form of particulates which are at least 95% by mass in the size range of 100 μm to 1000 μm with an average size in the range of 400 to 800 μm.

The term "simulated gastric fluid/water (1:8)" and the equivalent term "SGF/water (1:8)", as used herein, refer to a solution prepared according to the method described in Example 4.

As used herein, the "media uptake ratio" or "MUR" of a crosslinked polymer is a measure of the ability of a crosslinked polymer to absorb a specified aqueous medium according to the equation:

$$MUR=(W_{swollen}-W_{dry})/W_{dry}$$

where $W_{dry}$ is the weight of the initial dry crosslinked polymer sample and $W_{swollen}$ is the weight of the crosslinked polymer at equilibrium swelling. Unless otherwise noted, a reference herein to media uptake ratio or MUR refers to the value obtained in SGF/water (1:8) according to the method described in Example 5. It is to be understood that the units for MUR values reported herein are g/g.

As used herein, the "elastic modulus" or G' is determined for a crosslinked polymer swollen in SGF/water (1:8) according to the method described in Example 5.

As used herein, the "tapped density" of a sample is determined according to the method described in Example 5.

As used herein, the "water content" or the "loss on drying" of a sample is determined according to the method described in Example 5.

The citric acid crosslinked carboxymethylcelluloses of the invention can be used in methods for treating overweight or obesity, reducing food or calorie intake, or achieving or maintaining satiety in a subject. Crosslinked carboxymethylcellulose of the invention can also be used to improve glycemic control and to treat or prevent diabetes in a subject. The methods comprise the step of administering an effective amount of a citric acid crosslinked carboxymethylcellulose of the invention to the stomach of a subject, preferably by oral administration, for example, by causing the subject, such as a mammal, including a human, to swallow the citric acid crosslinked carboxymethylcellulose, optionally in combination with ingestion of a volume of water. Upon contacting water or aqueous stomach contents, the citric acid crosslinked carboxymethylcellulose swells and occupies stomach volume decreasing the capacity of the stomach for food and/or the rate of food absorption. When ingested in combination with food, the citric acid crosslinked carboxymethylcellulose increases the volume of the food bolus without adding to the calorie content of the food. The citric acid crosslinked carboxymethylcellulose can be ingested by the subject prior to eating or in combination with food, for example, as a mixture of the citric acid crosslinked carboxymethylcellulose with food.

The subject can be, for example, a human subject for whom weight loss will bring health benefits, such as human who is overweight, with a body mass index of 25 to 29.9, or obese, with a body mass index of 30 or higher. The subject can also be a human of normal weight, with a body mass index of 18.5 to 24.9, but at risk of unhealthy weight increase. A human subject can also have one or more other conditions or comorbidities, such as prediabetes, diabetes or heart disease, in addition to being overweight or obese. For example, the subject can have one or more of the following: hypertension, such as blood pressure of 140/90 mm Hg or higher; high LDL cholesterol; low HDL cholesterol, for example less than 35 mg/dL; high triglycerides, for example higher than 250 mg/dL; high fasting blood glucose, for example, ≥100 mg/dL; a family history of premature heart disease; physical inactivity; and cigarette smoking.

In one embodiment, the human subject is prediabetic, as determined by one or more of fasting glucose level, A1C level and oral glucose tolerance test, according to the criteria established by the American Diabetes Association (*Diabetes Care* 2004, 27:S15-35). For example, a prediabetic subject can have a fasting blood glucose level of 100 mg/dL to 125.9 mg/dL, an A1C level of 5.7 to 6.4% and/or an oral glucose tolerance test result of 140 to 199 mg/dL. Preferably, the prediabetic patient has a fasting blood glucose level of 100 mg/dL to 125.9 mg/dL.

In another embodiment, the human subject is diabetic, as determined by one or more of fasting glucose level, A1C level and oral glucose tolerance test. For example, a diabetic subject can have a fasting blood glucose level of 126 mg/dL or higher, an A1C level of 6.5% or higher and/or an oral glucose tolerance test result of 200 mg/dL or higher. Preferably, the diabetic patient has a fasting blood glucose level of 126 mg/dL or higher.

In another embodiment, the subject has metabolic syndrome, as diagnosed using the criteria set forth by the American Heart Association in 2004 (Grundy S M, et al., Circulation, 2004; 109:433-438). According to these guidelines, a subject is diagnosed with metabolic syndrome if at least three of the following five conditions are present: (1) elevated waist circumference (men: >40 inches; women: >35 inches); (2) elevated triglycerides (150 mg/dL or higher); (3) reduced HDL cholesterol (men: less than 40 mg/dL; women: less than 50 mg/dL); (4) elevated blood pressure (130/85 mm Hg or higher) or use of medication for hypertension; (5) elevated fasting glucose (≥100 mg/dL) or use of medication for hyperglycemia.

In another embodiment, the subject has a fasting glucose level of about 90 mg/dL or higher or about 92 or 93 mg/dL or higher. Subjects with fasting glucose levels in this range include those with normal fasting glucose levels (90 to under 100 mg/dL), prediabetes (100-125 mg/dL) and diabetes (126 mg/dL or higher).

The citric acid crosslinked carboxymethylcellulose is preferably administered in combination with water. The amount of water administered is preferably an amount effective to swell the citric acid crosslinked carboxymethylcellulose in the stomach of the subject. In one embodiment, at least about 100 mL of water per gram of crosslinked carboxymethylcellulose is administered. The water can be administered concomitant with or following administration of the pharmaceutical composition.

In one embodiment, the citric acid crosslinked carboxymethylcellulose is administered prior to or with a meal, for example, up to 2 hours, 1 hour or 0.5 hour prior to the meal.

The citric acid crosslinked carboxymethylcellulose can be ingested alone, in a mixture with liquid or dry food or as a component of a food or edible matrix, in a dry, partially swollen or fully swollen state, but is preferably ingested in a state of hydration which is significantly below its fluid capacity, more preferably the citric acid crosslinked carboxymethylcellulose is ingested in a substantially anhydrous state, that is, about 10% or less water by weight. The citric acid crosslinked carboxymethylcellulose can be formulated for oral administration in a capsule, sachet or tablet or suspension. When administered in a substantially anhydrous form, the volume of the stomach taken up by the citric acid crosslinked carboxymethylcellulose will be significantly greater than the volume of the citric acid crosslinked carboxymethylcellulose ingested by the subject. The citric acid crosslinked carboxymethylcelluloses of the invention can also take up volume and/or exert pressure on the wall of the small intestine by moving from the stomach into the small intestine and media uptake. Preferably, the citric acid crosslinked carboxymethylcellulose will remain swollen in the small intestine for a period of time sufficient to inhibit the intake of food by the subject, before shrinking sufficiently for excretion from the body. The time sufficient to inhibit the intake of food by the subject will generally be the time required for the subject to eat and for the ingested food to pass through the small intestine; Such shrinking can occur, for example, by degradation through loss of cross-links, releasing fluid and decreasing in volume sufficiently for excretion from the body.

The data presented in Example 6 show that hydrogels prepared as described herein provide a greater barrier to the diffusion of glucose compared to hydrogels prepared with a lower viscosity carboxymethylcellulose. In addition, Example 9 shows that swollen crosslinked carboxymethylcelluloses prepared as described herein have rheological properties similar to those of masticated food. Following oral administration, these materials therefore are expected to mimic food as they pass through the digestive tract. For example, these materials may mimic the undigested food to which the intestine is exposed following gastric bypass, which is thought to play a role in regulation of glucose in bypass patients (Saeidi N. et al., Science 2013, 341(6144): 406-10). Thus, the crosslinked carboxymethylcellulose of the invention may enhance glycemic control through multiple mechanisms.

The citric acid crosslinked carboxymethylcelluloses of the invention exhibit pH-dependent media uptake due to the presence of ionic groups attached to the polymer backbone, with greater media uptake observed at higher pH than at lower pH. Thus, such a polymer will not swell significantly in the stomach unless food and/or water is present to raise the pH of the stomach contents and will move into the small intestine. When ingested with food, the citric acid crosslinked carboxymethylcellulose preferably swells initially in the stomach, shrinks when the stomach is emptied of food and the pH drops and then moves from the stomach to the small intestine. In the higher pH environment of the small intestine the citric acid crosslinked carboxymethylcellulose will swell again, taking up volume in the small intestine and/or exerting pressure on the wall of the small intestine.

The citric acid crosslinked carboxymethylcellulose can optionally be administered in combination with a pH modifying agent, which is an agent which alters the pH of the microenvironment of the citric acid crosslinked carboxymethylcellulose, thereby modifying its ability to absorb fluids. For example, for citric acid crosslinked carboxymethylcelluloses comprising an anionic polymer, agents which increase the pH of the microenvironment can increase the swellability of the citric acid crosslinked carboxymethylcellulose. Suitable pH modifying agents for use with the citric acid crosslinked carboxymethylcelluloses of the invention include buffering agents, $H_2$ blockers, proton pump inhibitors, antacids, proteins, nutritional shakes, and combinations thereof. Suitable buffering agents and antacids include ammonium bicarbonate, sodium bicarbonate, calcium carbonate, calcium hydroxide, aluminium hydroxide, aluminium carbonate, magnesium carbonate, magnesium hydroxide, potassium bicarbonate, potassium carbonate, potassium hydroxide, sodium carbonate, sodium hydroxide and combinations thereof. Suitable $H_2$ blockers include cimetidine, ranitidine, famotidine, nizatidine and combinations thereof. Suitable proton pump inhibitors include omeprazole, lansoprazole, esomeprazole, pantoprazole, abeprazole, and combinations thereof.

The citric acid crosslinked carboxymethylcellulose of the invention can be administered to the subject in the form of a tablet, a capsule a sachet or other formulation suitable for oral administration. The tablet or capsule can further include one or more additional agents, such as a pH modifying agent, and/or a pharmaceutically acceptable carrier or excipient. The citric acid crosslinked carboxymethylcellulose can also be administered as a component of a food or a beverage, such as is described in WO 2010/059725, incorporated herein by reference in its entirety.

In one embodiment, the present invention provides a pharmaceutical composition comprising a citric acid crosslinked carboxymethylcellulose of the invention. The pharmaceutical composition can comprise the citric acid crosslinked carboxymethylcellulose as an active agent, optionally in combination with a pharmaceutically acceptable excipient or carrier. For example, the pharmaceutical composition can be intended for oral administration to treat obesity, provide enhanced satiety, improve glycemic control, treat or prevent diabetes or aid in weight management.

In another embodiment, the pharmaceutical composition comprises the citric acid crosslinked carboxymethylcellulose in combination with another active agent.

In one embodiment, the invention provides a pharmaceutical composition comprising a citric acid crosslinked carboxymethylcellulose of the invention having (1) a loss on drying of 10% (wt/wt) or less; and (2) are in the form of particulates which are at least 95% by mass in the size range of 100 µm to 1000 µm with an average size in the range of 400 to 800 µm. The citric acid crosslinked carboxymethylcellulose can be, for example, encapsulated in a capsule, such as a hard or soft gelatin capsule. Preferably, the composition does not comprise a disintegrant. In certain embodiments, the capsule is a hard gelatin capsule size 00EL, and under the conditions described in Example 7 (37° C. in SGF/water 1:8), the capsule disintegrates within 7.5 minutes and the citric acid crosslinked carboxymethylcellulose is homogeneously hydrated within 15 minutes.

The scope of the present invention includes the use of the citric acid crosslinked carboxymethylcelluloses of the invention as an absorbent material in products which are capable of absorbing water and/or aqueous solutions and/or which are capable of media uptake when brought into contact with water and/or an aqueous solution. The citric acid crosslinked carboxymethylcellulose of the present invention may be used as an absorbent material in the following fields, which are provided as non-limiting examples: dietary supplements (for example, as the bulking agents in dietary supplements for hypocaloric diets capable of conferring a sensation of lasting satiety being retained into the stomach for a limited period of time, or as water and low molecular weight compounds supplements, such as mineral salts or vitamins, to be included into drinks in a dry or swollen form); in agricultural products, for example, in devices for the controlled release of water and/or nutrients and/or phytochemicals, particularly for cultivation in arid, deserted areas and in all cases where it is not possible to carry out frequent irrigation; such products, mixed in a dry form with the soil in the areas surrounding the plant roots, absorb water during irrigation and are capable of retaining it, releasing it slowly in certain cases, together with the nutrients and phytochemicals useful for cultivation; in personal hygiene and household absorbent products, such as, for example, as the absorbent core in diapers, sanitary napkins and the like; in toys and devices, such as for example in products which are capable of significantly changing their size once brought into contact with water or an aqueous solution; in the biomedical field, for example, in biomedical and/or medical devices such as absorbent dressings for the treatment of highly exudative wounds, such as ulcers and/or burns, or in slow-release polymeric films suitable to slowly release liquids adapted for use in ophthalmology; in the body fluid management field, for example, for controlling the amount of liquids in an organism, for example in products capable of promoting the elimination of fluids from the body, such as, for example, in the case of edema, CHF (congestive heart failure), dialysis; and in home cleaning products.

The above-mentioned products, containing a citric acid crosslinked carboxymethylcellulose of the present invention as the absorbent material, also fall within the scope of the invention.

The invention further includes the use of any of the citric acid crosslinked carboxymethylcelluloses of the invention in medicine. Such use includes the use of a crosslinked carboxymethylcellulose in the preparation of a medicament for the treatment of obesity or any medical disorder or disease in which calorie restriction has a therapeutic, palliative or prophylactic benefit.

The citric acid crosslinked carboxymethylcelluloses of the invention have advantages over previously described crosslinked carboxymethylcellulose, such as those exemplified in US 2013/0089737. As set forth in the examples, citric acid crosslinked carboxymethylcelluloses produced using high viscosity carboxymethylcellulose have comparable media uptake ratio and tapped density compared to those produced with lower viscosity carboxymethylcellulose while having a significantly higher G'. As demonstrated in the examples, the citric acid crosslinked carboxymethylcellulose of the invention provides a stronger barrier to glucose diffusion, faster and more homogeneous swelling and consistent capsule opening without the need for a disintegrant compared to citric acid crosslinked carboxymethylcellulose produced with lower viscosity carboxymethylcellulose. The citric acid crosslinked carboxymethylcellulose of the invention is also sensitive to changes in pH of the external environment. Oral dosage forms including the citric acid crosslinked carboxymethylcellulose would therefore be expected to result in slower gastric emptying, enhanced glycemic control, more consistent dosing and more rapid onset of action compared to prior art crosslinked carboxymethylcellulose. The improved elasticity of these materials may also play a fundamental role in activating metabolic pathways in the lower GI tract for improved weight loss (Saeidi N, et al., Science 2013, 341(6144):406-10).

EXAMPLES

Example 1

Preparation of Crosslinked Carboxymethylcellulose-Laboratory Scale

Crosslinked carboxymethylcellulose was produced using the following protocol.
Materials
Carboxymethylcellulose sodium salt (CMCNa): Aqualon 7H4FM (Ashland Inc.), viscosity range 7600-9000 cps (1% wt/wt solution in water at 25° C.)
Citric acid
Purified water Purified water (3 kg) was placed to a mixing bowl. 0.36 g citric acid was added and the mixture was sitrred until the citric acid was completely dissolved. 180 g CMCNa was slowly added to the citric acid solution and the resulting suspension was mixed continuously for 18 hours using a mixer with a flat blade.

A portion of the material from the mixing bowl was placed with a spoon on a silicone sheet on a stainless steel tray. Using a plastic spatula the material was spread until it appeared uniform without spilling over the edges. This was repeated using additional trays until all of the material was spread on trays.

The trays in an oven set to 50° C. When drying was complete (about 23 hours) the trays were removed from the oven. In this and the other examples set forth herein, drying is considered complete when the loss on drying, determined as described in Example 5, is 10% or less.

The sheets of dried material remaining after drying were broken into smaller pieces that could be easily ground. The grinding was started by inserting the material slowly into a collection bin to insure that the material did not overheat on grinding. At the end of the grinding, the material was sieved between 100 and 1600 μm.

The ground material (50 g) was placed in a small aluminum dish. The aluminum dish was placed in an oven heated to 120 (±1) ° C. to induce crosslinking. The dish was removed from the oven after 4 hours.

The crosslinked material (10 g) was placed in a beaker with 1500 g water and stirred at room temperature for 3 hours. The resulting swollen material was filtered and the water was removed using a vacuum pump. The ratio of swelling obtained was 55.6 g/g.

The washed material was placed on a plastic tray. Using a plastic spatula, the material was spread evenly in the trays. The trays were placed in an oven set to 50 (±1) ° C. After drying was complete (20h), the trays were removed from the oven.

The dried material was inserted slowly into the collection bin of a grinder to insure that it would not overheat on grinding. The ground material was sieved between 100 and 1000 μm.

The media uptake ratio of the resulting powder, determined as set forth in Example 5, was 73. The G' was determined as described in Example 5 and was 2028 Pa.

Example 2

Preparation of Crosslinked Carboxymethylcellulose-Large Scale

Crosslinked carboxymethylcellulose was produced on a large scale using the following protocol.
Materials
Carboxymethylcellulose sodium salt (CMCNa): AQUALON™ 7H4 FM (Ashland Inc.), viscosity range 7600-9000 cps (1% wt/wt solution in water at 25° C.)
Citric acid
Purified water To 5 kg of CMCNa in a mixing bowl was added 21 kg of water and mixing was begun. After 10 minutes a solution of 5 g citric acid in 21 kg of water was under constant mixing for 10 minutes. 21 kg of water was then added and mixed for 10 minutes. Finally, a solution of 5 g citric acid in 21 kg of water was add and the mixture was mixed for 200 minutes.

A portion of the material from the mixing bowl was placed with a spoon on a silicone sheet on a stainless steel tray. Using a plastic spatula the material was spread until it appeared uniform without spilling over the edges. This was repeated using additional trays until all of the material was spread on trays.

The trays were placed in an oven set to 70° C. When drying was complete (48 hours) the trays were removed from the oven.

The sheets of dried material were broken into smaller pieces that could be easily ground. The grinding was started by inserting the material slowly into a collection bin to insure that the material did not overheat on grinding. At the end of the grinding, the material was sieved between 100 and 1600 μm.

The ground material was placed in a stainless steel drum. The drum was placed in an oven heated to 120 (±1) ° C. to induce crosslinking. The drum was removed from the oven after 4 hours.

1 kg of the crosslinked material was placed in a stainless steel tank with 150 kg water with constant stirring at room temperature for 4 hours. The resulting swollen material was filtered using a sieve and the water was removed using a vacuum pump. The ratio of swelling obtained was 73.2 g/g.

The washed material was placed on plastic trays. Using a plastic spatula, the material was spread evenly in the trays. The trays were placed in an oven set to 70 (±1) ° C. After drying was complete (72 h), the trays were removed from the oven.

The dried material was inserted slowly into the collection bin of a grinder to insure that it would not overheat on grinding. The ground material was sieved between 100 and 1000 μm.

The media uptake ratio of the resulting powder, determined as set forth in Example 5, was 70.29 g/g. The G' determined as described in Example 5 was 2967 Pa.

Citric acid crosslinked carboxymethylcellulose was also prepared using the general method above, but with a total of 15.0 g citric acid. The materials resulting from these syntheses were characterized as provided in Tables 1 and 2 below. In each case, a portion of the carboxymethylcellulose/citric acid composite was crosslinked.

TABLE 1

| Run | Viscosity of CMC (cps, 1% aqueous solution at 25° C.) | Weight after 1st sieving [g] (100-1600 μm) | LOD before crosslink (wt %) | Crosslink time [h] | Washing ratio [kg/L] | Weight before Washing [g] | Weight after Washing [kg] |
|---|---|---|---|---|---|---|---|
| 1 | 9000 | 4717.8 | 3.40 | 4 | 1/150 | 1079.8 | 87.00 |
| 2 | 9000 | 4756.5 | 3.96 | 4.5 | 1/150 | 1070.0 | 65.00 |
| 3 | 8900 | 4775.4 | 4.47 | 4 | 1/150 | 1084.0 | 96.60 |
| 4 | 8900 | 4755.7 | 3.68 | 4.5 | 1/150 | 1270.0 | 90.30 |
| 5 | 7600 | 4878.2 | 6.38 | 4 | 1/150 | 2186.0 | 202.00 |
| 6 | 7600 | 4874.0 | 5.37 | 4.5 | 1/150 | 2190.0 | 182.90 |

TABLE 2

| Run | Swelling in washing | Weight after 2nd sieving [g] (100-1000 μm) | Yield [%] | MUR | G' [Pa] | LOD (wt %) | Tapped density [g/mL] |
|---|---|---|---|---|---|---|---|
| 1 | 79.6 | 791.7 | 63.34% | 87.50 | 2025 | 4.07 | 0.7 |
| 2 | 59.7 | 893.2 | 71.46% | 61.66 | 3252 | 9.86 | 0.7 |
| 3 | 88.1 | 733.3 | 58.66% | 80.28 | 2749 | 3.18 | 0.6 |
| 4 | 70.1 | 1037.3 | 69.85% | 56.81 | 3396 | 7.82 | 0.7 |
| 5 | 91.4 | 1233.0 | 49.32% | 82.01 | 2195 | 3.74 | 0.6 |
| 6 | 82.5 | 1673.2 | 66.93% | 66.47 | 2570 | 11.17 | 0.6 |

Example 3

Preparation of Crosslinked Carboxymethylcellulose with Lower Viscosity Carboxymethylcellulose Purified water (80 kg) was added to a 140 liter Hobart mixer and agitated. Citric acid (14.4 g) was added to the water and dissolved. CMCNa (4.8 kg; 7H3SXF (AQUA-LON™)), having a viscosity of 1000-2600 cps as a 1% (wt/wt) solution in water at 25° C., was then added to the solution and the resulting mixture was agitated at room temperature for 4 hours. The resulting solution was added to 30 stainless steel trays (2700 g solution per tray). The trays were placed in a SHELLAB oven at 70° C. for 48 hours. After the desiccation the material was ground by means of a cutting mill (Retsch cutting mill) equipped with a 2 mm screen. The granulated material was then sieved between 0.1-1.6 mm and then placed into the stainless-steel drum for the cross-linking reaction in the Salvis Thermocenter TC240 oven at 120° C. for 7 hours. The crosslinked polymer hydrogel thus obtained was washed with purified water for 3 hours under mild agitation to remove the unreacted reagents. The washing stage allows the media uptake of the crosslinked polymer by increasing the relaxation of the network thus increasing the media uptake capacity of the final material obtained after a further desiccation step. After the washing the material was placed on trays and placed in the oven at 70° C. for 72 h to dry. The dry material was then ground and sieved to a particle size from 100 μm to 1000 μm.

Example 4

Preparation of Simulated Gastric Fluid/Water (1:8)

Reagents used for preparation of SGF/water (1:8) solution are purified water, sodium chloride, 1M hydrochloric acid and pepsin.
1. To a 1 L graduated cylinder pour about 880 mL of water.
2. Place the cylinder on a magnetic stirrer, add a magnetic bar and start stirring.
3. Begin monitoring the pH of the water with a pH meter.
4. Add a sufficient amount of 1M hydrochloric acid to bring the pH to 2.1±0.1.
5. Add 0.2 g NaCl and 0.32 g pepsin. Leave the solution to stir until complete dissolution.
6. Remove the magnetic bar and the electrode from the cylinder.
7. Add the amount of water required to bring the volume to 900 mL.

Example 5

Characterization of Carboxymethylcellulose and Crosslinked Carboxymethylcellulose (A) Determination of Viscosity of Carboxymethylcellulose Solutions
Equipment and Materials:
Constant temperature water bath.
Glass Bottle, 500 ml with a cap, diameter of the neck at least 80 mm.
Brookfield Viscometer, model Myr VR3000 (ECO208) or equivalent equipped with:
Spindle L4
Thermal printer (PRP-058GI)
Mechanical overhead stirrer with anchor stainless steel stirrer.
Chain clamp to secure glassware.
Lab spatula.
Aluminum crucible
Analytical balance, capable of weighing to the nearest 0.001 g.
Calibrated balance, capable of weighing, to the nearest 0.1 g.
Purified water
Procedure
Preparation of Test Samples:
Prepare three CMC/water solutions as described below:
1. Measure the moisture content of CMC powder as described in [B] below.

2. Calculate the amount of water required using the equation:

$$\text{water required}[g]=3*(99-LOD\text{average}).$$

3. Weigh the needed amount of water for preparing the CMC solution into a beaker.
4. Pour roughly half of this water into the bottle, with the rest of the water remaining in the beaker.
5. Place and tie up the bottle under the stirrer motor with a chain clamp.
6. Insert the stirrer.
7. Mix the sample to assure uniformity.
8. Weigh 3.0±0.1 g of CMC powder.
9. Pour the powder in small amounts into the bottle while mixing at low speed (ca. 600 rpm).
10. Mix for 2 minutes and set the mixing speed to 1000 rpm.
11. Mix for no less than 10 minutes but no more than 30 minutes.
12. Add the remaining water.
13. Mix for additional 30 minutes.
14. If the CMC is not dissolved completely, continue stirring.
15. Once all the CMC is dissolved remove the anchor stainless steel stirrer and place the cap on the bottle.
16. Place the flask in the constant temperature bath, at 25.0° C. ±0.1° C., for at least 30 minutes but no longer than one hour.
17. Shake the bottle vigorously for 10 seconds. The solution is ready to be tested.

Viscosity Measurement:
1. Determine viscosity of each sample according to the instructions for the viscometer. Allow rotation of spindle for exactly 3 minutes.
2. Determine the average viscosity of the three solutions.

(B) Determination of Loss on Drying
The moisture content of a carboxymethylcellulose or cross-linked carboxymethylcellulose is determined according to USP <731>, Loss on Drying.

Instruments/Equipment
Moisture Analyzer Radwag, Model WPS 50S
Lab Spatula
Aluminum crucible
Desiccator with silica gel Procedure
1. Place the sample in the desiccator for at least 12 hours.
2. Place the aluminum crucible on the scale pan of the moisture analyzer and tare the balance.
3. Accurately weigh 1.000±0.005 g of a sample in the aluminum crucible. The initial weight of the sample is $W_i$.
4. Set the Moisture Analyzer to heat the sample at 105° C. for 30 minutes under ambient pressure and moisture.
5. Turn on the Moisture Analyzer and run the LOD program (30 min at 105° C.).
6. Weigh the sample. The final weight of the sample is $W_f$. The LOD value is determined according to the equation:

$$LOD=(W_i-W_f)/W_i\times100\%.$$

The Loss on Drying is determined in triplicate, and the reported LOD is the average of the three values.

(C) Determination of Particle Size Range
Equipment and Materials:
Sieve Shaker Retsch, Model AS 200 basic
Stainless Steel Sieves with mesh sizes 1000 μm and 100 μm
Aluminum weighing pan
Laboratory stainless steel spatula
Calibrated balance, capable of weighing to the nearest 0.1 g.

Procedure:
1. Weigh the empty sieves and the aluminum pan to the nearest 0.1 g.
2. Weigh out 40.0±0.1 g of powder.
3. Stack the test sieves with sizes 1000 and 100 μm with larger pore size on the top and the smaller at the bottom. Assemble the aluminum pan at the bottom of the nest.
4. Pour the sample into the 1000 μm sieve, at the top of the stack.
5. Place this stack between the cover and the end pan of the shaker, so that the sample remains in the assembly.
6. Turn on the main switch of the shaker.
7. Set knob UV2 of the shaker for continuous operation.
8. Turn the knob MN2 of the shaker to the right to increase the vibration height until 50.
9. Shake this stack with the shaker for 5 minutes.
10. Disassemble the sieve and reweigh each sieve.
11. Determine the percentage weight of test specimen in each sieve as described in paragraph 8.
12. After measuring the weight of the full and empty test sieves, determine, by difference, the weight of the material inside each sieve.
13. Determine the weight of material in the collecting pan in a similar manner.
14. Use the weight of sample contained in each sieve and in the collecting pan to calculate the % distribution with the following equation:

$$Wx\%=Wx/W\text{sample}*100\%$$

where:
Wx %=sample weight in each sieve or in the collecting pan, in percentage where the index "x" is:
">1000" for particle size bigger than 1000
"100-1000" for particle size between 100 and 1000
"<100" for particle size smaller than 100
Wsample=initial weight of test specimen.

(D) Determination of Tapped Density
Equipment and materials:
100 mL glass graduated cylinder
100 mL glass beaker
Lab spatula
Mechanical tapped density tester, Model JV 1000 by Copley Scientific
Calibrated balance capable of weighing to the nearest 0.1 g.

Procedure:
1. Weigh out 40.0±0.1 grams of test sample. This value is designated M.
2. Introduce the sample into a dry 100 mL glass graduated cylinder.
3. Carefully level the powder without compacting and read the unsettled apparent volume, V0, to the nearest graduated unit.
4. Set the mechanical tapped density tester to tap the cylinder 500 times initially and measure the tapped volume, V500, to the nearest graduated unit.
5. Repeat the tapping 750 times and measure the tapped volume, V750, to the nearest graduated unit.
6. If the difference between the two volumes is less than 2%, V750 is the final tapped volume, Vf, otherwise repeat in increments of 1250 taps, as needed, until the difference between succeeding measurements is less than 2%.

Calculations:
Calculate the Tapped Density, DT, in gram per mL, by the formula:

$$DT=M/Vf$$

where:

M=Weight of sample, in grams, rounded off to the nearest 0.1 g.

Vf=Final volume, in mL.

(E) Determination of Media Uptake Ratio in SGF/Water (1:8)

The media uptake ratio of a crosslinked carboxymethylcellulose in SGF/water (1:8) is determined according to the following protocol.

1. Place a dried fritted glass funnel on a support and pour 40.0±1.0 g of purified water into the funnel.
2. Wait until no droplets are detected in the neck of the funnel (about 5 minutes) and dry the tip of the funnel with an absorbent paper.
3. Place the funnel into an empty and dry glass beaker (beaker #1), place them on a tared scale and record the weight of the empty apparatus ($W_{tare}$).
4. Put a magnetic stir bar in a 100 mL beaker (beaker #2); place beaker #2 on the scale and tare.
5. Add 40.0±1.0 g of SGF/Water (1:8) solution prepared as described above to beaker #2.
6. Place beaker #2 on the magnetic stirrer and stir gently at room temperature.
7. Accurately weigh 0.250±0.005 g of crosslinked carboxymethylcellulose powder using a weighing paper ($W_{in}$).
8. Add the powder to beaker #2 and stir gently for 30±2 min with the magnetic stirrer without generating vortices.
9. Remove the stir bar from the resulting suspension, place the funnel on a support and pour the suspension into the funnel, collecting any remaining material with a spatula.
10. Allow the material to drain for 10±1 min.
11. Place the funnel containing the drained material inside beaker #1 and weigh it ($W'_{fin}$).

The Media Uptake Ratio (MUR) is calculated according to:

$$MUR=(W_{fin}-W_{in})/W_{in}.$$

$W_{fin}$ is the weight of the swollen hydrogel calculated as follows:

$$W_{fin}=W'_{fin}-W_{tare}.$$

$W_{in}$ is the weight of the initial dry sample.

The MUR is determined in triplicate for each sample of crosslinked carboxymethylcellulose and the reported MUR is the average of the three determinations.

(F) Determination of Elastic Modulus

The elastic modulus (G') is determined according to the protocol set forth below. The rheometer used is a Rheometer Discovery HR-1 (5332-0277 DHR-1) by TA Instruments or equivalent, equipped with a Peltier Plate; a Lower Flat plate Xhatch, 40 mm diameter; and an Upper Flat plate Xhatch, 40 mm diameter.

1. Put a magnetic stir bar in a 100 mL beaker.
2. Add 40.0±1.0 g of SGF/Water (1:8) solution prepared as described above to the beaker.
3. Place the beaker on the magnetic stirrer and stir gently at room temperature.
4. Accurately weigh 0.250±0.005 g of crosslinked carboxymethylcellulose powder using a weighing paper (Wm).
5. Add the powder to the beaker and stir gently for 30±2 min with the magnetic stirrer without generating vortices.
6. Remove the stir bar from the resulting suspension, place the funnel on a support and pour the suspension into the funnel, collecting any remaining material with a spatula.
7. Allow the material to drain for 10±1 min.
8. Collect the resulting material.
9. Subject the material to a sweep frequency test with the rheometer and determine the value at an angular frequency of 10 rad/s.

The determination is made in triplicate. The reported G' value is the average of the three determinations.

(G) Comparison of Properties of Crosslinked Carboxymethylcellulose Prepared with High Viscosity and Lower Viscosity Carboxymethylcellulose The table below shows the ranges of MUR, G' and tapped density obtained for multiple samples of citric acid crosslinked carboxymethylcellulose prepared by the methods described in Examples 2 (High Viscosity) and 3 (Lower Viscosity). The measurements described below were made using samples of crosslinked carboxymethylcellulose with the following characteristics 1) a loss on drying of 10% or less; and (2) in the form of particulates which are at least 95% by mass in the size range of 100 μm to 1000 μm with an average size in the range of 400 to 800 μm.

TABLE 3

|  | Lower Viscosity | High Viscosity |
| --- | --- | --- |
| MUR (g/g) | 75-108 | 60-85 |
| G' (Pa) | 1600-590 | 3400-2100 |
| Tapped density (g/cm³) | 0.7-0.8 | 0.6-0.7 |

The results show that the materials prepared from high viscosity carboxymethylcellulose have MUR values and tapped densities comparable to the materials prepared from lower viscosity carboxymethylcellulose. Notably, the materials prepared from high viscosity carboxymethylcellulose have a significantly higher G' than the materials prepared from lower viscosity carboxymethylcellulose.

Example 6

Inhibition of Glucose Diffusion

Hydrogel A was prepared as described in Example 3.

Hydrogel B

Hydrogel B was prepared as described below. This method is substantially similar to the method described in Example 2.

Purified water (80 kg) was added to a 140 L Hobart mixer and agitated. Citric acid (9.6 g) was added to the water and dissolved. CMCNa (Aqualon 7H4 FM (Ashland Inc.), viscosity range 6000-9000; 4.8 kg) was then added to the solution and the resulting mixture was agitated at room temperature for 4 hours. The resulting solution was added to 30 stainless steel trays (2,700 g solution per tray). The trays were placed in a SHELLAB oven at 70° C. for 48 hours. After the desiccation the material was ground by means of a cutting mill (Retsch cutting mill) equipped with a 2 mm screen. The granulated material was then sieved between 0.1-1.6 mm and then placed into the stainless-steel drum for the cross-linking reaction in the Salvis Thermocenter TC240 oven at 120° C. for 4 hours. The crosslinked polymer hydrogel thus obtained was washed with purified water for 3 hours under mild agitation to remove the unreacted reagents. The washing stage allows the media uptake of the crosslinked polymer by increasing the relaxation of the network thus increasing the media uptake capacity of the final material obtained after a further desiccation step. After the washing the material was placed on trays and placed in the oven at 70° C. for 72 h to dry. The dry material was then ground and sieved to a particle size from 100 μm to 1000 μm.

The ability of glucose to diffuse through swollen crosslinked carboxymethylcellulose was determined using the following procedure:
1. Solubilize glucose in water overnight at a concentration of 1000 mg/dL.
2. Prepare the dialysis tube washing it in a beaker with purified water for 3 hours, and replacing the water every hour.
3. Put 0.5% (w/V) dry crosslinked carboxymethylcellulose in 80 mL of glucose solution and stir for 30 minutes.
4. Pour the hydrated gel and the glucose solution from step 3 into the open end of the dialysis tube and seal with two dialysis tubing closures.
5. Place the dialysis tube in the plastic bag containing purified water at 37° C.
6. Measure the glucose concentration of the dialysate at 15 minutes, 30 minutes and every 30 minutes to 300 minutes using an Accu-Chek™ glucometer.
Results Hydrogel A was produced according to the method of Example 3, above, which is substantially as described in Example 7 of US Published Application 2013/0089737, incorporated herein by reference in its entirety, starting with AQUALON™ 7H3 SXF carboxymethylcellulose sodium (Ashland Inc.), which has a viscosity of 1,000 to 2,800 cps as a 1% (wt/wt) solution in water at 25° C. Hydrogel B was produced as described above, starting with AQUALON™ 7H4FM carboxymethylcellulose sodium (Ashland Inc.), having a viscosity of 6000 to 9000 cps as a 1% (wt/wt) solution in water at 25° C.

Figure 2:
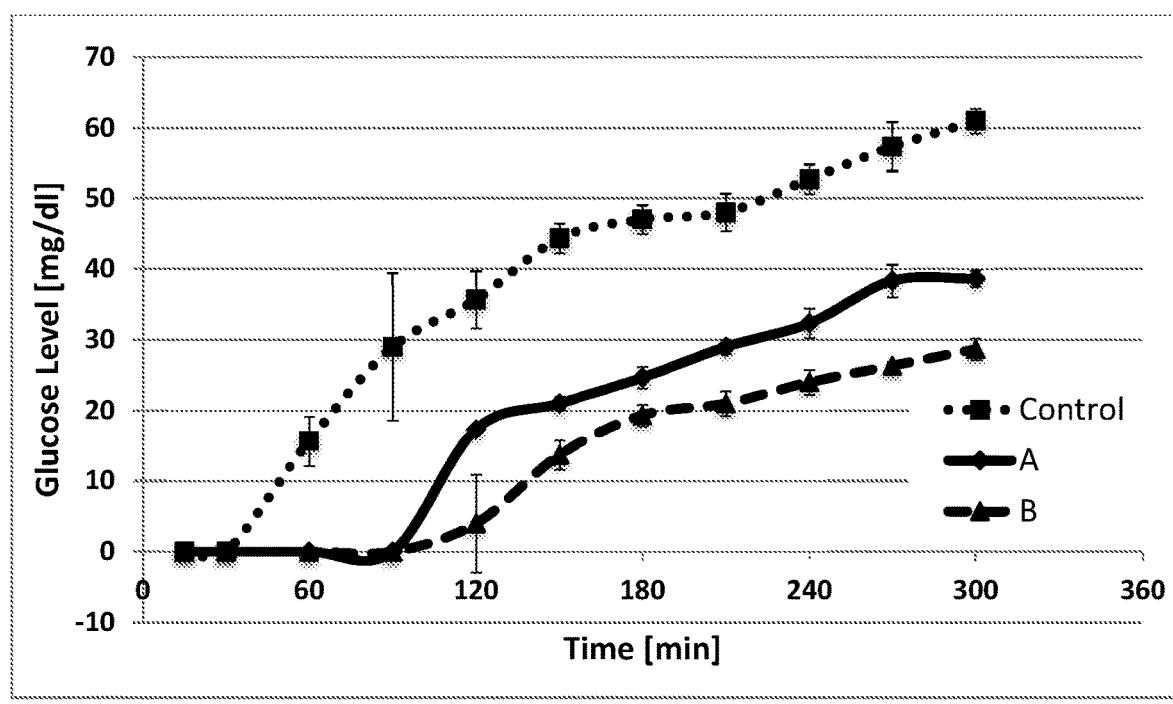
FIG. 2 is a graph showing the dialysate glucose concentration for tests performed with Hydrogel A and Hydrogel B as a function of time as described in Example 6.

FIG. 2 is a graph showing the dialysate glucose concentration for Hydrogel A and Hydrogel B as a function of time. The results show that glucose diffuses across the dialysis membrane significantly more rapidly for Hydrogel A than for Hydrogel B. This suggests that Hydrogel B would be more effective than Hydrogel A at inhibiting glucose diffusion to the intestinal wall in vivo, and thus, more effective at slowing the rate of glucose absorption.

Example 7

Opening of Crosslinked Carboxymethylcellulose Filled Capsules

The disintegration of hard size 00EL gelatin capsules filled with crosslinked carboxymethylcellulose was determined according to the procedure described in USP <701>, incorporated herein by reference in its entirety.
Apparatus
pH meter, Model PC 700 by Eutech Instrument or equivalent
Analytical balance, capable of weighing, to the nearest 0.01 g
Weighing paper
Lab spatula
1 L graduated cylinder
Magnetic stirrer
Disintegration tester, model DTG 1000 by Copley Scientific (Equipment Code: EC0067), which is equipped with:
A one piece PETG water bath
External thermo-stirrer heater with over-temperature/low water-level safety cut-offs
Temperature measurement by Pt100 probe
A 1000 mL-Beaker
Basket rack assembly
1. Place SGF/Water (1:8) solution prepared as in Example 3 in the 1000 mL beaker. The volume of the fluid in the vessel is such that at the highest point of the upward stroke the wire mesh remains at least 15 mm below the surface of the fluid and descends to not less than 25 mm from the bottom of the vessel on the downward stroke. At no time should the top of the basket-rack assembly become submerged.
2. Turn on the heater on the disintegration bath and set the temperature to 37° C.
3. To perform the test, ensure that the water bath temperature is 37° C. ±2° C., that the temperature of the media in the test vessel is correct and that the disintegration basket to contain the dosage units under test is mounted on the hanger bar.
4. Drop one capsule into each of the 6 capsule compartments in the baskets.
5. Set the disintegration tester to run for 7.5 min.
6. At the end of the set time the basket will be lifted from the vessel. Examine the status of capsules and determine how many have disintegrated. If some capsules have not disintegrated, the tester can be run for an additional 7.5 min. and the extent of disintegration determined again.

The Capsules Disintegration Test was performed according to USP <701>on Hydrogels A and B as described in Example 6. The test is designed to quantify the correct disintegration of capsules in simulated gastric media (SGF/water 1:8). The test was run for 15 min with an intermediate check timepoint at 7.5 min. The operator considered the capsule to be completely disintegrated only if there was an absence of pieces of the starting capsule in the basket. The operator also collected information regarding the presence of aggregates or lumps at the end of the test by pouring the material onto a stainless tray.

Figure 3:
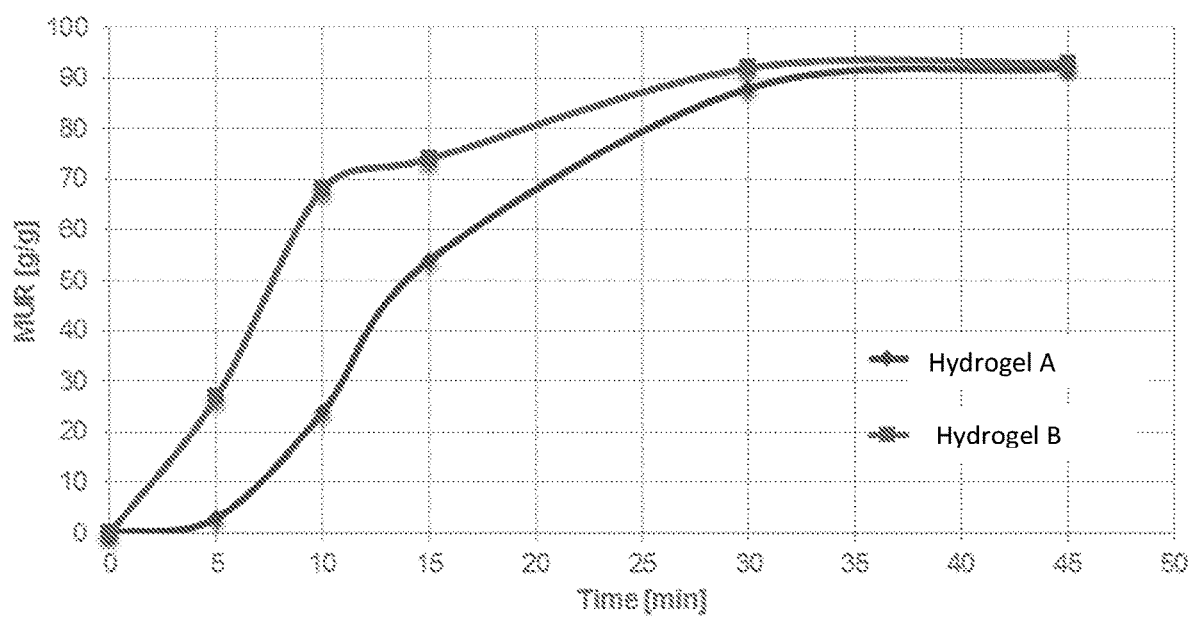
FIG. 3 is a graph of media uptake ratio (MUR) versus time following capsule disintegration for Hydrogel A and Hydrogel B as described in Example 7.

For both Hydrogels A (including fumarate as disintegrant) and B (without disintegrant), the gelatin capsules were disintegrated after 7.5 minutes, but the samples showed different hydration. In particular, after 15 minutes, Hydrogel A includes an aggregation of particles that are not completely hydrated; in contrast, after 15 minutes Hydrogel B is homogeneously hydrated. The media uptake ratio of both hydrogels was determined at 5, 10, 15, 30, and 45 minutes following capsule disintegration. The results, which are set forth in FIG. 3, show that Hydrogel B swells much more rapidly than Hydrogel A and, in particular, is significantly more swollen over the first 15 minutes post-disintegration. Both hydrogels reach equilibrium swelling at about 30 minutes following disintegration.

Example 8

Determination of Swelling Kinetics

The hydration kinetics of Hydrogels A and B (Example 6) in SGF/water (1:8) were determined (i) using viscosimetry and (ii) by measuring the media uptake ratio over time as described below.
(A) Viscometry
Apparatus:
Rheometer, Discovery HR-1 by TA Instruments equipped with:
Starch Pasting Cell with temperature control.
Helical rotor (bob diameter 32.40 mm; bob length 12 mm).
Flow Peak Hold Test Parameters:
Angular velocity: 6.28 rad/s (velocity applied to the sample by the motor at each measurement).
Duration: 3600 s.
Temperature: 37° C.
Solution: SGF/Water (1/8) pH 2.1.
Concentration of Hydrogels A and B: 1% w/w.

Figure 4:
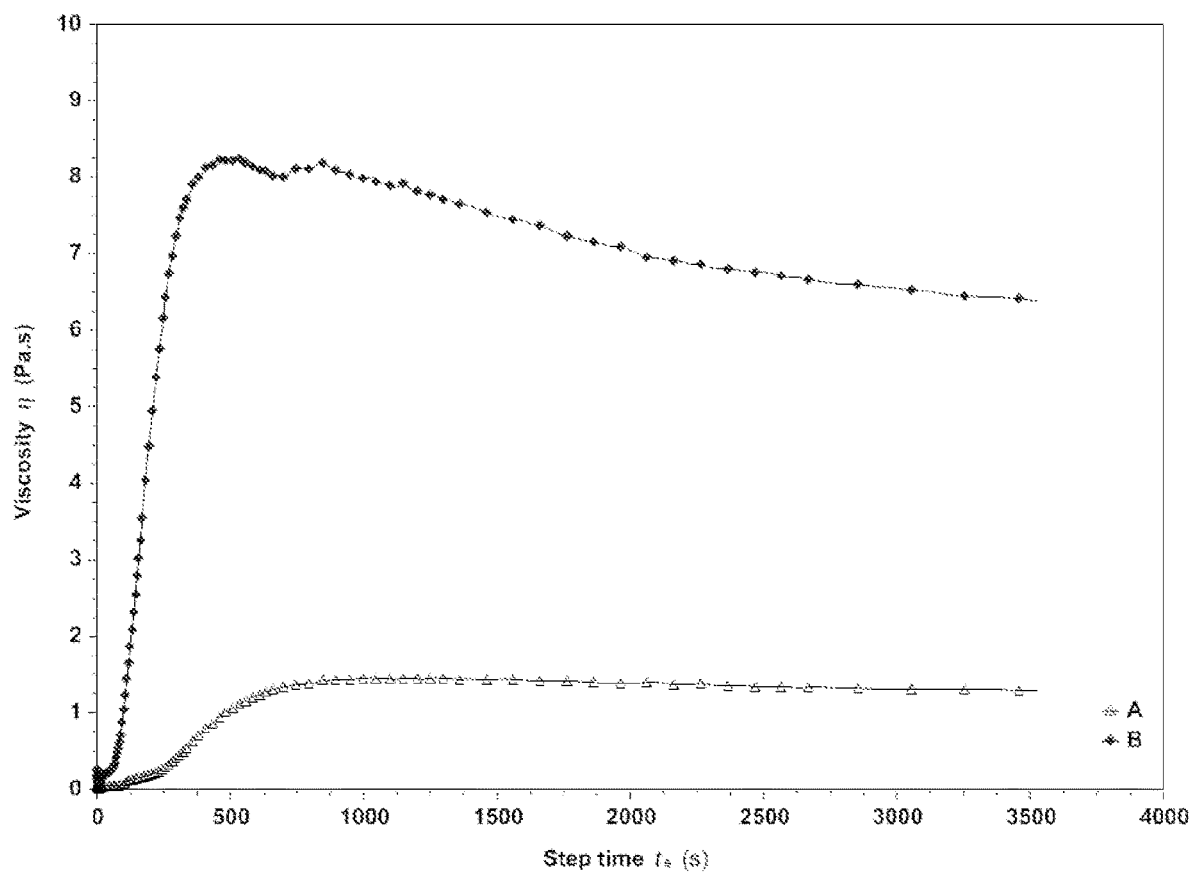
FIG. 4 is a graph of viscosity versus time for Hydrogel A and Hydrogel B as described in Example 8.

The results of this study are shown in FIG. 4, which is a graph of viscosity versus time. The viscosity of Hydrogel B increases much more rapidly than that of Hydrogel A, and reaches a much greater value than Hydrogel A.

(B) Media Uptake Ratio Versus Time

Figure 5:
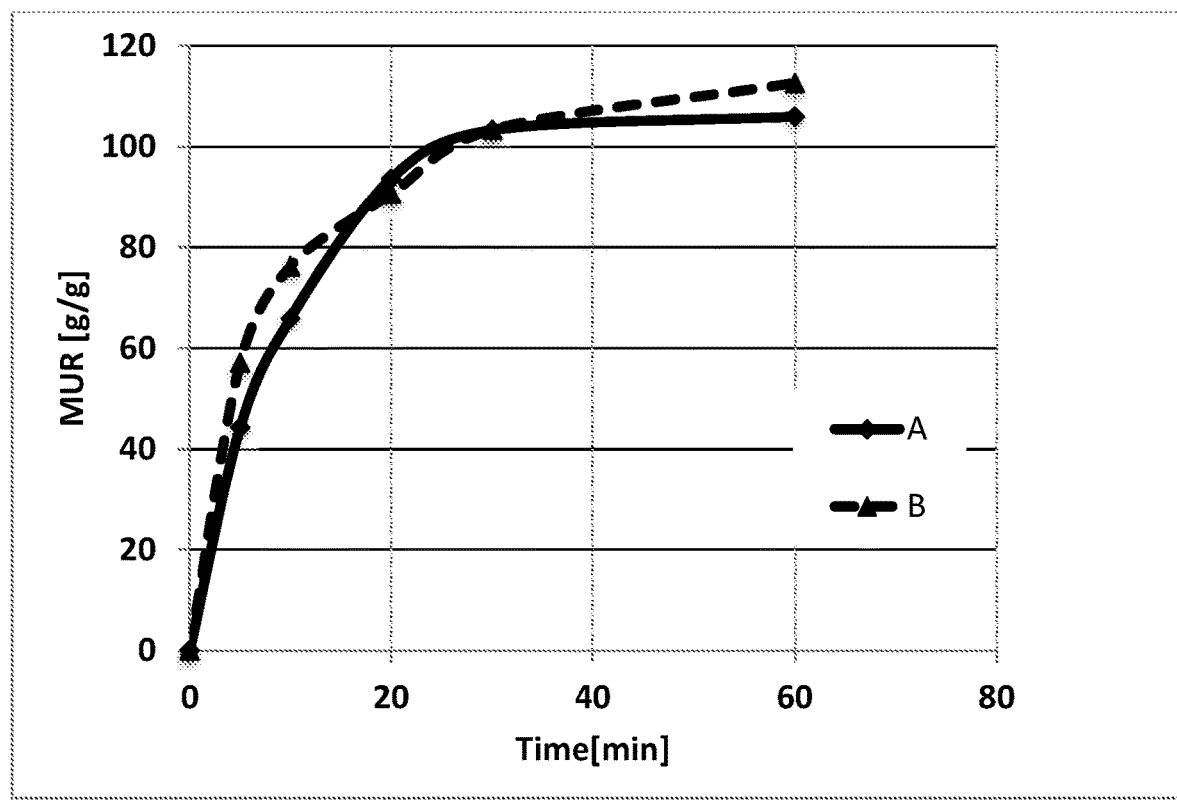
FIG. 5 is a graph of media uptake ratio versus time for Hydrogel A and Hydrogel B as described in Example 8.

The media uptake ratios of Hydrogel A and Hydrogel B were determined as described in Example 5(D) except that measurements were taken at 5, 10, 20, 30 and 60 minutes. The results shown in FIG. 5 indicate that Hydrogel B absorbs SGF/water (1:8) more rapidly over the first 10 to 15 minutes than Hydrogel A.

(C) G' Versus Time

Figure 6:
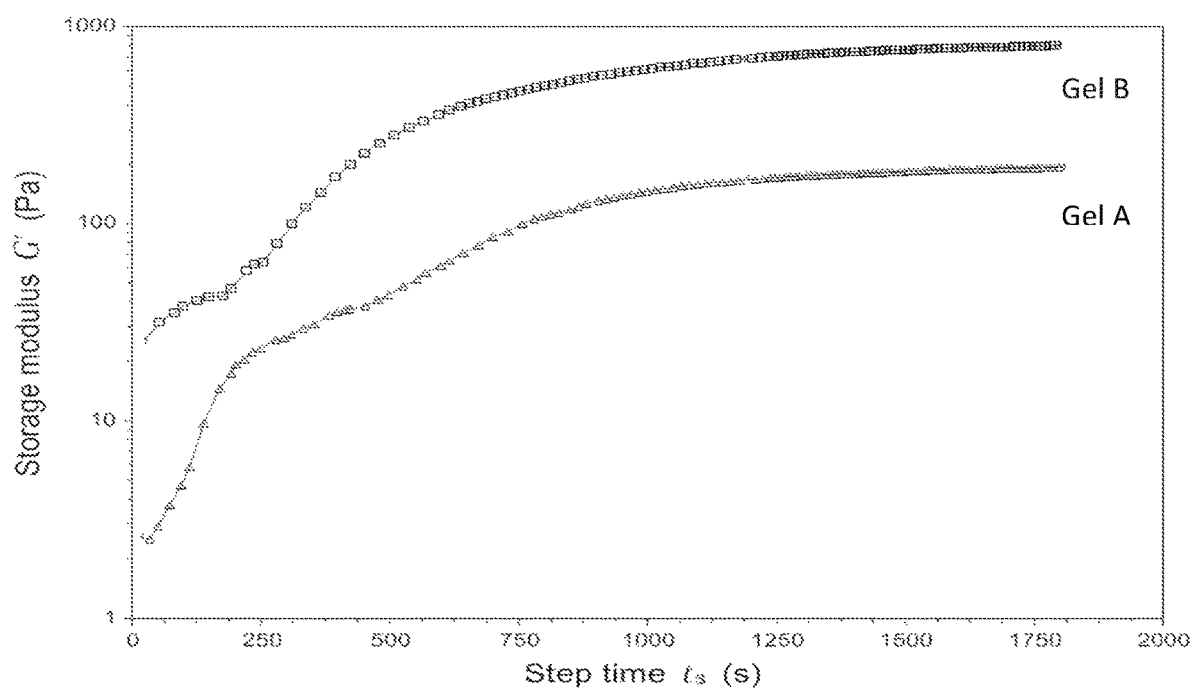
FIG. 6 is a graph of G' versus time for Hydrogel A and Hydrogel B as described in Example 8.

This experiment was performed using the apparatus and method described in (A) above, but with a frequency of 10 rad/sec. The results are shown in FIG. 6, which is a graph of G' versus time for Hydrogel A and Hydrogel B. Hydrogel B has a significantly higher G' than Hydrogel A at all time points. This difference in G' is particularly significant at early time points.

Example 9

Comparison of Swollen Hydrogels to Masticated Food

G' determined for 124 lots of crosslinked carboxymethylcellulose prepared according to Example 3 (low viscosity CMC) and 36 lots prepared according to Example 2 (high viscosity CMC). In addition, the G' of a masticated food bolus consisting of a Big Mac™ hamburger, an order of French fries and 350 mL of a medium consisting of 50 mL pure SGF and 300 mL of the soft drink Sprite™ was measured in triplicate. The G' values were determined as described in Example 5, and the average G' determined for each sample type is shown in Table 4 below.

TABLE 4

| Sample | Average G' |
| --- | --- |
| Low viscosity CMC | 1050 Pa |
| High viscosity CMC | 2070 Pa |
| Masticated food | 1957 Pa |

The results show that the hydrogels prepared with the high viscosity CMC have a G' which is much closer to that of masticated food than the hydrogels prepared with lower viscosity CMC.

Example 10

Determination of Polymer Molecular Weight and Polydispersity Index

The weight average molecular weight and polydispersity index of samples of sodium carboxymethylcellulose (CMC) were determined using the method set forth below. Data were analyzed using a computer with data analysis software.
Gel Permeation Chromatography Apparatus
1) Guard Column:
Brand: Agilent Technologies PL-aquagel-OH Guard column
Size: 50×7.5 mm (length×diameter); 8 μm (particles size).
2) Column:
Brand: Agilent Technologies PL-aquagel-OH Mixed-H
Size: 300×7.5 mm (length×diameter); 8 μm (particles size).
Preparation of Aqueous Eluent
1. In 1 L graduated cylinder pour 500 ml of purified water.
2. Weigh 17 g ±0.05 g of Sodium nitrate and pour it in the graduated cylinder.
3. Weigh 1.56 g ±0.05 g of Sodium Phosphate Monobasic dihydrate and pour it in the graduated cylinder.
4. Add purified water in the cylinder up to 1 L.
5. Insert a stirrer bar in the cylinder and cover it with parafilm.
6. Put the cylinder on the magnetic stirrer and stir until complete dissolution of the salt.
7. Measure the pH of the solvent and adjust to pH 7±1 if necessary with 0.2 N sodium hydroxide.
8. Filter 200 ml of the eluent using a syringe filter (mesh size 0.2 μm) and store it in a covered beaker in order to prepare the sample for GPC analyses.
Gel Permeation Chromatography
Calibration:
Set the temperature of the chromatography apparatus to 35° C.
Set up a ramp for the eluent flow up to 1 ml/min and allow the RID to stabilize.
Prepare Pullulan standards for calibration as follows:
Dissolve each standard in the filtered eluent at 0.15% w/v, according to the following sequence: 667, 6000, 21700, 48800, 210000, 805000, 1330000, 2560000 [g/mol]
Allow the standards to completely dissolve in the eluent and inject the standards one at a time. Create a calibration curve. The stability of the apparatus is verified over time using the retention time of the Internal Standard: D-Sorbitol 182 g/mol (0.15% w/w in the eluent)
Analysis of Sodium Carboxymethylcellulose:
Each CMC sample is prepared by dissolving 0.015 g of CMC powder in 10 mL of eluent in a closed vial. The samples are prepared in triplicate.
Allow CMC samples to dissolve in the eluent by stirring overnight at room temperature.
Inject each sample.
Data are analyzed using an interfaced computer and appropriate data analysis software (Empower3, Waters Corporation) to determine Mw and polydispersity index (integration algorithm: ApexTrack).
Results The results of the analyses of three lots each of AQUALON 7H4FM and 7H3SXF are set forth in Table 5 below.

TABLE 5

| Sample | Viscosity (cps, 1% in water at 25° C.) | Mw (Dalton) | Polydispersity Index |
| --- | --- | --- | --- |
| A. 7H4FM | 9000 | $3.06 \times 10^6$ | 5.9 |
| B. 7H4FM | 8900 | $3.15 \times 10^6$ | 5.2 |
| C. 7H4FM | 7600 | $3.16 \times 10^6$ | 6 |
| D. 7H3SXF | 2100 | $2.70 \times 10^6$ | 9.5 |
| E. 7H3SXF | 2320 | $2.69 \times 10^6$ | 8.5 |
| F. 7H3SXF | 2100 | $2.72 \times 10^6$ | 16.0 |

These results show that the AQUALON™ 7H4FM samples have significantly greater viscosity and Mw than the 7H3SXF samples. The 7H4FM samples also have a significantly lower polydispersity index, indicating the narrower molecular weight distribution and greater molecular weight homogeneity of this material compared to the 7H3 SXF samples.

Example 11

Determination of Swelling and G' in Simulated Intestinal Fluid

Preparation of Simulated Intestinal Fluid
Simulated Intestinal Fluid (SIF) Test Solution, known formally as 'Intestinal fluid, simulated TS (Test Solution)', was prepared according to the method of United States Pharmacopeia 33-28NF (2010). Monobasic potassium phosphate (6.8 g) was dissolved in 250 mL of water and then 77 mL of 0.2 N sodium hydroxide and 500 mL of water were added to this solution. 10.0 g of pancreatin was then added and the resulting solution was adjusted with 0.2 N sodium hydroxide or 0.2 N hydrochloric acid to a pH of 6.8±0.1 and finally diluted with water to a volume 1000 mL.

The G' and media uptake ratio in both SGF/water 1:8 and simulated intestinal fluid (SIF) were determined for two lots of crosslinked carboxymethylcellulose prepared according to the method of Example 2 (Hydrogel B) and two lots prepared according to the method of Example 3 (Hydrogel A). The G' and MUR in simulated intestinal fluid were determined as described in Example 5 except that simulated intestinal fluid was substituted for SGF/water 1:8. The results are shown in Table 6 below.

TABLE 6

| Material | MUR SGF/Water 1:8 | MUR SIF | G' SGF/Water 1:8 (Pa) | G' SIF (Pa) |
|---|---|---|---|---|
| Hydrogel A (Lot 1) | 78 | 58 | 1336 | 977 |
| Hydrogel B (Lot 1) | 75 | 66 | 2221 | 1357 |
| Hydrogel A (Lot 2) | 83 | 60 | 986 | 750 |
| Hydrogel B (Lot 2) | 70 | 60 | 2341 | 1734 |

The results show that materials produced using high viscosity carboxymethylcellulose have significantly greater G' when swollen in either SIF or SGF/water 1:8 compared to materials produced using low viscosity carboxymethylcellulose. Surprisingly, while the MUR of the low viscosity material in SGF/water 1:8 was slightly greater than that for the high viscosity material, in SIF the two types of materials were essentially equivalent. Notably, going from SGF/water 1:8 to SIF, the MUR decrease for the high viscosity material was significantly less than the decrease for the low viscosity material.

These results are important because the presence of swollen hydrogel in the small intestine plays a fundamental role as far as mechanisms that affect glycemic control, especially the creation of a diffusion barrier for slowing glucose absorption by increasing the elasticity and viscosity of ingested food. In addition, higher elastic response of the small intestine content may contribute to achieving an effect similar to that of a gastric bypass (Saeidi N, et al., Science 2013, 341(6144):406-10).

Intestinal fluids have high ionic strength, which significantly decreases the hydrogel swelling due to a decrease in the Donnan type swelling contribution (see A. Sannino and L. Nicolais, *Polymer*, 46(13) 4676-4685 (2005)). The Donnan contribution promotes hydrogel swelling by means of an osmotic pressure generated between the inside and the outside of the hydrogel, allowing water to penetrate the hydrogel and depends, in a linear fashion, on the difference in concentration of ionic charges between the inside and the outside of the hydrogel; the higher the difference, the higher the Donnan contribution.

Hydrogels made from carboxymethylcellulose with high viscosity and low polydispersity have unexpectedly better hydration rates combined with higher G' compared to CMC-based hydrogels described in the prior art and also have better combined G'/MUR performance in small intestine models such as described in Example 5. This improved performace is surprising considering the higher ionic strength of the small intestine fluids.

While this invention has been particularly shown and described with references to preferred embodiments thereof, it will be understood by those skilled in the art that various changes in form and details may be made therein without departing from the scope of the invention encompassed by the appended claims.

We claim:

1. A pharmaceutical composition in a form suitable for oral administration comprising a crosslinked carboxymethylcellulose, which is produced by a method comprising crosslinking carboxymethylcellulose with citric acid, wherein said carboxymethylcellulose has a viscosity as a 1% (wt/wt) aqueous solution at 25° C. of greater than 6000 cps and a polydispersity index less than 8, wherein said crosslinked carboxymethylcellulose is in the form of particles which are at least 80% by mass in the size range of 100 μm to 1000 μm and the particles have an average particle size in the range of 400 to 800 μm; and a pharmaceutically acceptable carrier or excipient.

2. The pharmaceutical composition of claim 1, wherein the crosslinked carboxymethylcellulose is in the form of particles which are at least 95% by mass in the size range of 100 μm to 1000 μm and has a loss on drying of 10% or less (wt/wt).

3. The pharmaceutical composition of claim 2, wherein the crosslinked carboxymethylcellulose has a tapped density from about 0.5 g/mL to about 0.9 g/mL.

4. The pharmaceutical composition of claim 3, wherein the crosslinked carboxymethylcellulose has a tapped density from about 0.65 g/mL to about 0.75 g/mL.

5. The pharmaceutical composition of claim 1 wherein the viscosity is from 7800 to 11000 cps and the polydispersity index is from about 4 to about 7.

6. The pharmaceutical composition of claim 1, wherein the carboxymethylcellulose has a degree of substitution of about 0.65 to about 0.95.

7. The pharmaceutical composition of claim 1, wherein the crosslinked carboxymethylcellulose is produced by a method comprising the steps of
   (a) preparing an aqueous solution of carboxymethylcellulose having a viscosity as a 1% (wt/wt) aqueous solution at 25° C. of at least 6000 cps and a polydispersity index of less than 8, wherein the concentration of the carboxymethylcellulose is at least 1% by weight relative to water, and an amount of citric acid from about 0.05% to about 0.5% by weight relative to the weight of the carboxymethylcellulose;
   (b) agitating the solution;
   (c) drying the solution to form a carboxymethylcellulose/citric acid composite;
   (d) comminuting the composite to produce composite particles;
   (e) heating the composite particles at a temperature of at least about 80° C., thereby cross-linking the carboxymethylcellulose with the citric acid and forming the crosslinked carboxymethylcellulose;
   (f) washing the crosslinked carboxymethylcellulose of step (e) with water;
   (g) drying the washed crosslinked carboxymethylcellulose and
   (h) comminuting the crosslinked carboxymethylcellulose product of step (g).

8. The pharmaceutical composition of claim 7, wherein the concentration of the carboxymethylcellulose in step (a)

is from about 4% to about 8% by weight relative to water, and the citric acid concentration in step (a) is from about 0.15% to about 0.3% by weight relative to the weight of the carboxymethylcellulose.

9. The pharmaceutical composition of claim 8, wherein the concentration of the carboxymethylcellulose in step (a) is about 6% by weight relative to water, and the citric acid concentration in step (a) is about 0.2% by weight relative to the weight of the carboxymethylcellulose.

10. The pharmaceutical composition of claim 1, in the form of a sachet, tablet or capsule.

11. A method of treating overweight or obesity in a subject in need thereof, comprising the step of orally administering to the subject an effective amount of the pharmaceutical composition of claim 1.

12. The method of claim 11, further comprising orally administering to the subject an amount of water effective to swell the crosslinked carboxymethylcellulose.

13. The method of claim 12, wherein the subject has a body mass index of at least 30.

14. The method of claim 11, wherein the pharmaceutical composition is administered up to 2 hours prior to a meal.

15. A method of enhancing glycemic control in a subject in need thereof, comprising the step of orally administering to the subject an effective amount of the pharmaceutical composition of claim 1.

16. The method of claim 15, wherein the subject is prediabetic or diabetic.

17. The method of claim 15, wherein the pharmaceutical composition is administered from 0 to 1 hour prior to a meal.

18. A method of treating diabetes in a subject in need thereof, comprising the step of orally administering to the subject an effective amount of the pharmaceutical composition of claim 1.

19. The method of claim 18, further comprising orally administering to the subject an amount of water effective to swell the crosslinked carboxymethylcellulose.

* * * * *